(12) United States Patent
Corum

(10) Patent No.: US 12,396,655 B2
(45) Date of Patent: Aug. 26, 2025

(54) ROBUST AND COMPUTATIONALLY EFFICIENT MISSING POINT AND PHASE ESTIMATION FOR FID SEQUENCES

(71) Applicant: Champaign Imaging LLC, Shoreview, MN (US)

(72) Inventor: Curtis A. Corum, Shoreview, MN (US)

(73) Assignee: Champaign Imaging LLC, Shoreview, MN (US)

( * ) Notice: Subject to any disclaimer, the term of this patent is extended or adjusted under 35 U.S.C. 154(b) by 185 days.

(21) Appl. No.: 18/288,267

(22) PCT Filed: Apr. 29, 2022

(86) PCT No.: PCT/US2022/027149
§ 371 (c)(1),
(2) Date: Oct. 25, 2023

(87) PCT Pub. No.: WO2022/232658
PCT Pub. Date: Nov. 3, 2022

(65) Prior Publication Data
US 2024/0206759 A1 Jun. 27, 2024

Related U.S. Application Data

(60) Provisional application No. 63/182,658, filed on Apr. 30, 2021.

(51) Int. Cl.
*G01V 3/00* (2006.01)
*A61B 5/00* (2006.01)
(Continued)

(52) U.S. Cl.
CPC .......... *A61B 5/055* (2013.01); *A61B 5/0042* (2013.01); *A61B 5/7203* (2013.01);
(Continued)

(58) Field of Classification Search
CPC .............. G01R 33/287; G01R 33/4835; G01R 33/5608; A61B 2090/374
(Continued)

(56) References Cited

U.S. PATENT DOCUMENTS

| | | |
|---|---|---|
| 2010/0253341 A1 | 10/2010 | Corum et al. |
| 2014/0077810 A1 | 3/2014 | Grodzki |

(Continued)

FOREIGN PATENT DOCUMENTS

| | | | |
|---|---|---|---|
| WO | 2019094436 | 5/2019 | |
| WO | WO-2019094436 A1 * | 5/2019 | ............. A61B 5/055 |
| WO | 2019232437 | 12/2019 | |

OTHER PUBLICATIONS

International Search Report and the Written Opinion of the International Searching Authority for International Application No. PCT/US2022/027149 mailed Aug. 18, 2022, (6 pages).

(Continued)

*Primary Examiner* — Walter L Lindsay, Jr.
*Assistant Examiner* — Frederick Wenderoth
(74) *Attorney, Agent, or Firm* — Dicke, Billig & Czaja, PLLC

(57) ABSTRACT

A system includes a machine readable storage medium storing instructions and a processor to execute the instructions. The processor executes the instructions to receive magnetic resonance imaging (MRI) data of a patient obtained via a free induction decay (FID) sequence, each FID of the FID sequence indicating missing or corrupted points at the beginning of the FID. The processor executes the instructions to replace the missing or corrupted points of each FID with estimated points to generate a corrected FID sequence. The processor executes the instructions to estimate a phase that minimizes an imaginary DC value of each corresponding FID.

20 Claims, 16 Drawing Sheets

(51) Int. Cl.
    *A61B 5/055* (2006.01)
    *G01R 33/48* (2006.01)
    *G01R 33/561* (2006.01)
    *G06F 16/23* (2019.01)
    *G06T 11/00* (2006.01)

(52) U.S. Cl.
    CPC ....... *G01R 33/4816* (2013.01); *G01R 33/561* (2013.01); *G06F 16/2365* (2019.01); *G06T 11/006* (2013.01); *A61B 2576/026* (2013.01)

(58) Field of Classification Search
    USPC ......................................................... 324/309
    See application file for complete search history.

(56) References Cited

U.S. PATENT DOCUMENTS

| | | |
|---|---|---|
| 2014/0107469 A1 | 4/2014 | Gjesdal et al. |
| 2015/0115956 A1 | 4/2015 | Ackerman et al. |
| 2017/0356973 A1 | 12/2017 | Wheaton |

OTHER PUBLICATIONS

Pipe, J. G. & Menon, P., "Sampling Density Compensation in MRI: Rationale and an Iterative Numerical Solution," Magnetic Resonance in Medicine, vol. 41, pp. 179-186 (1999).

Stoch, G. and Olejniczak, Z., "Missing first points and phase artifact mutually entangled in FT NMR data—noniterative solution," Journal of Magnetic Resonance, vol. 173, pp. 140-152 (2005).

Brunner, D. O.; Furrer, L.; Weiger, M.; Baumberger, W.; Schmid, T.; Reber, J.; Dietrich, B. E.; Wilm, B. J.; Froidevaux, R. & Pruessmann, K. P., Accepted manuscript, "Symmetrically Biased T/R switches for NMR and MRI with Microsecond Dead Time," Journal of Magnetic Resonance, pp. 28. (2015). DOI: http://dx.doi.org/10.1016/j.imr.2015.12.016.

Rollins, J. D.; Collins, J. S. & Holden, K. R. (2010). United States Head Circumference Growth Reference Charts: Birth to 21 years, The Journal of pediatrics 156: 907-913.e2. PMID: 20304425.

Hoult, D. I. (1979). Fast recovery, high sensitivity NMR probe and preamplifier for low frequencies, Review of Scientific Instruments 50: 193-200. PMID: 18699468.

Marjanska, M.; Waks, M.; Snyder, C. J. & Vaughan, J. T. (2008). Multinuclear NMR investigation of Probe Construction Materials at 9.4T., Magn Reson Med 59: 936-938. PMID: 18383292.

Corum, C. A.; Idiyatullin, D.; Snyder, C. J. & Garwood, M. (2015). Gap Cycling for SWIFT, Magn Reson Med 73: 677-682. PMID: 24604286.

Weiger, M.; Pruessmann, K. P. & Hennel, F. (2011). MRI with Zero Echo Time: Hard versus Sweep Pulse Excitation, Magn Reson Med., pp. 1-11. PMID: 21381099.

Lauterbur, P. C. (1973). Image Formation by Induced Local Interactions: Examples Employing Nuclear Magnetic Resonance, Nature 242: 190-191. PMID: 2663289.

Hafner, S. (1994). Fast Imaging in Liquids and Solids with the Back-Projection Low Angle ShoT (BLAST) Technique, Magn Reson Imaging 12: 1047-1051. PMID: 7997092.

Edelstein, W. A.; Hutchison, J. M. S.; Johnson, G. & Redpath, T. (1980). Spin warp NMR imaging and applications to human whole-body imaging, Phys. Med. Biol. 25: 751-756. PMID: 7454767.

Crémillieux, Y.; Briguet, A. & Deguin, A. (1994). Projection-Reconstruction Methods: Fast Imaging Sequences and Data Processing, Magn Reson Med 32: 23-32. PMID: 8084234.

Botto, R. E.; Cody, G. D.; Dieckman, S. L.; French, D. C.; Gopalsami, N. & Rizo, P. (1996). Three-dimensional magnetic resonance microscopy of materials, Solid State Nucl Magn Reson 6: 389-402. PMID: 8902960.

Herman, G. T.; Roberts, D. & Axel, L. (1992). Fully three-dimensional reconstruction from data collected on concentric cubes in Fourier space: implementation and a sample application to MRI., Phys Med Biol 37: 673-687. PMID: 1565696.

Peters, D. C.; Derbyshire, J. A. & McVeigh, E. R. (2003). Centering the Projection Reconstruction Trajectory: Reducing Gradient Delay Errors, Magnetic Resonance in Medicine 50: 1-6. PMID: 12815671.

Jung, Y.; Jashnani, Y.; Kijowski, R. & Block, W. F. (2007). Consistent Non-Cartesian Off-Axis MRI Quality: Calibrating and Removing Multiple Sources of Demodulation Phase Errors, Magn Reson Med 57: 206-212. PMID: 17139618.

Atkinson, I. C.; Lu, A. & Thulborn, K. R. (2009). Characterization and Correction of System Delays and Eddy Currents for MR Imaging with Ultrashort Echo-Time and Time-Varying Gradients, Magn Reson Med 62: 532-537. PMID: 19353662.

Herrmann, K.-H.; Krämer, M. & Reichenbach, J. R. (2016). Time Efficient 3D Radial UTE Sampling with Fully Automatic Delay Compensation on a Clinical 3T MR Scanner, PLoS One 11: pp. 1-16. PMID: 26975051.

Johnson, K. M.; Lum, D. P.; Turski, P. A.; Block, W. F.; Mistretta, C. A. & Wieben, O. (2008). Improved 3D Phase Contrast MRI with Off-Resonance Corrected Dual Echo VIPR, Magnetic Resonance in Medicine 60: 1329-1336. PMID: 19025882.

Knoll, F.; Schwarzl, A.; Diwoky, C. & Sodickson, D. K. (2014). gpuNUFFT—An open source GPU library for 3D regridding with direct Matlab interface, Proc. Intl. Soc. Mag. Reson. Med. 22: 4297. PMID: https://github.com/andyschwarzl/gpuNUFFT.

Simmross-Wattenberg, F.; Rodríguez-Cayetano, M.; del-Val, J. R.; Martin-González, E.; Moya-Sáez, E.; Martin-Fernández, M. & Alberola-López, C. (2018). OpenCLIPER: an OpenCL-based C++ Framework for Overhead-Reduced Medical Image Processing and Reconstruction on Heterogeneous Devices, IEEE Journal of Biomedical and Health Informatics, pp. 1-8. PMID: https://arxiv.org/abs/1807.11830.

Chamberlain, R.; Etheridge, M.; Idiyatullin, D.; Corum, C.; Bischof, J. & Garwood, M. (2012). Measuring T1 in the presence of very high iron concentrations with SWIFT, Proc. Intl. Soc. Mag. Reson. Med. 20: 4368.

Phantom Test Guidance for Use of the Large MRI Phantom for the ACR MRI Accreditation Program, Large Phantom Guidance, pp. 1-28. (2018). PMID: https://www.acraccreditation.org/-/media/ACRAccreditation/Documents/MRI/LargePhantomGuidance.pdf.

Mortamet, B.; Bernstein, M. A.; Jack, Jr, C. R.; Gunter, J. L.; Ward, C.; Britson, P. J.; Meuli, R.; Thiran, J.-P.; Krueger, G. & , A. D. N. I. (2009). Automatic Quality Assessment in Structural Brain Magnetic Resonance Imaging, Magn Reson Med 62: 365-372. PMID: 19526493.

Somerville, L. H.; Bookheimer, S. Y.; Buckner, R. L.; Burgess, G. C.; Curtiss, S. W.; Dapretto, M.; Elam, J. S.; Gaffrey, M. S.; Harms, M. P.; Hodge, C.; Kandala, S.; Kastman, E. K.; Nichols, T. E.; Schlaggar, B. L.; Smith, S. M.; Thomas, K. M.; Yacoub, E.; Van Essen, D. C. & Barch, D. M. (2018). The Lifespan Human Connectome Project in Development: A large-scale study of brain connectivity development in 5-21 year olds, NeuroImage 183: 456-468. PMID: 30142446.

Watanabe, K.; Kakeda, S.; Igata, N.; Watanabe, R.; Narimatsu, H.; Nozaki, A.; Rettmann, D.; Abe, O. & Korogi, Y. (2016). Utility of real-time prospective motion correction (PROMO) on 3D T1-weighted imaging in automated brain structure measurements, Scientific reports 6: 38366. PMID: 27917950.

Maclaren, J.; Aksoy, M.; Ooi, M. B.; Zahneisen, B. & Bammer, R. (2018). Prospective Motion Correction Using Coil-Mounted Cameras: Cross-Calibration Considerations, Magnetic Resonance in Medicine 79: 1911-1921. PMID: 28722314.

Du, J.; Bydder, M.; Takahashi, A. M.; Carl, M.; Chung, C. B. & Bydder, G. M. (2011). Short T2 contrast with three-dimensional ultrashort echo time imaging, Magn Reson Imaging 29: 470-482. PMID: 21440400.

Corum, C. A.; Bauman, G.; Idiyatullin, D. S.; Hutter, D.; Everson, L. I.; Eberly, L. E.; Nelson, M. T.; Garwood, M.; Velikina, J. V. & Samsonov, A. A. (2015). High Spatial and Temporal Resolution Breast MRI with 3D Radial SWIFT Acquisition and Compressed Sensing MOCCO Reconstruction, (SWIFT-MOCCO), pp. 1. PMID: cbi15a.

Corum, C. A.; Benson, J. C.; Idiyatullin, D.; Snyder, A.; Snyder, C.; Hutter, D.; Everson, L.; Eberly, L. E.; Nelson, M. T. & Garwood, M. (2015). High Spatial and Temporal Resolution Breast DCE MRI

(56) References Cited

OTHER PUBLICATIONS with SWIFT (SWeep Imaging with Fourier Transformation): a pilot study, Radiology, p. 22. PMID: 25247405.

Chiang, J.-T. A.; Carl, M. & Du, J. (2014). Signal and contrast effects due to T2 decay during k-space readout of UTE (ultrashort TE) sequences, Magn Reson Imaging, pp. 1-11. PMID: 24457160.

Corum, C. A.; Kruger, S. & Magnotta, V. A., HEALPix View-order for 3D+time Radial Self-Navigated Motion-Corrected ZTE MRI, IEEE 17th International Symposium on Biomedical Imaging (ISBI), pp. 1-4 (2020). PMID: http://arxiv.org/pdf/1910.10276v2.

Kuethe, D. O.; Caprihan, A.; Lowe, I. J.; Madio, D. P. & Gach, H. M. (1999). Transforming NMR Data Despite Missing Points, J Magn Reson 139: 18-25. PMID: 10388580.

Beatty, P. J.; Nishimura, D. G. & Pauly, J. M. (2005). Rapid Gridding Reconstruction with a Minimal Oversampling Ratio, IEEE Transactions on Medical Imaging, 24: 799-808. PMID: 15959939.

Mitja, C.; Escofet, J.; Tacho, A. & Revuelta, R. (2011). Slanted Edge MTF, SE_MTF_2xNyquist.jar. pp. 3. PMID: https://imagej.nih.gov/ij/plugins/se-mtf/index.html.

Gerchberg, R. W. (1974). Super-resolution through error energy reduction, Optica Acta: International Journal of Optics 21: 709-720. PMID: ger74.

Papoulis, A. (1975). A new Algorithm in Spectral Analysis and Band-Limited Extrapolation, IEEE Transactions on Circuits and Systems, CAS-22: 735-742. PMID: pap75.

Jackson, J.; Macovski, A. & Nishimura, D. (1989). Low-Frequency Restoration, Magnetic Resonance in Medicine 11: 248-257. PMID: 2779415.

Yan, H. & Gore, J. C. (1990). An Efficient Algorithm for MR Image Reconstruction Without Low Spatial Frequencies, IEEE Transactions on Medical Imaging 9: 184-189. PMID: 18222763.

Wu, Y.; Dai, G.; Ackerman, J. L.; Hrovat, M. I.; Glimcher, M. J.; Snyder, B. D.; Nazarian, A. & Chesler, D. A. (2007). Water- and Fat-Suppressed Proton Projection MRI (WASPI) of Rat Femur Bone, Magnetic Resonance in Medicine 57: 554-567. PMID: 17326184.

Techawiboonwong, A.; Song, H. K. & Wehrli, F. W. (2008). In vivo MRI of submillisecond T(2) species with two-dimensional and three-dimensional radial sequences and applications to the measurement of cortical bone water, NMR Biomed 21: 59-70. PMID: 17506113.

Weiger, M.; Hennel, F. & Pruessmann, K. P. (2010). Sweep MRI with Algebraic Reconstruction, Magn Reson Med 64: 1685-1695. PMID: 20949600.

Rodts, S. & Bytchenkoff, D. (2013). Extrapolation and phase correction of non-uniformly broadened signals, Journal of Magnetic Resonance 233: 64-73. PMID: 23735873.

Grodzki DM, Jakob PM, Heismann B., Ultrashort Echo Time Imaging Using Pointwise Encoding Time Reduction With Radial Acquisition (PETRA). Magn Reson Med. 67: 510-8 (2012) doi: 10.1002/mrm.23017. Epub Jun. 30, 2011. PMID: 21721039. https://pubmed.ncbi.nlm.nih.gov/21721039/.

Schwarzl, Andreas, "Extension and Optimization of a GPU-Regridding framework for MP image reconstruction," Practical Report, TU Graz, pp. 1-24 (Jun. 2014).

Alibek, S.; Vogel, M.; Sun, W.; Winkler, D.; Baker, C. A.; Burke, M. & Gloger, H. (2014). Acoustic noise reduction in MRI using Silent Scan: an initial experience, Diagn Interv Radiol 20: 360-363. PMID: 24808439.

Bednarz, H. M. & Kana, R. K. (2018). Advances, challenges, and promises in pediatric neuroimaging of neurodevelopmental disorders, Neuroscience and biobehavioral reviews 90: 50-69. PMID: 29608989.

Barkovich, M. J.; Li, Y.; Desikan, R. S.; Barkovich, A. J. & Xu, D. (2019). Challenges in pediatric neuroimaging., NeuroImage, 185: 793-801. PMID: 29684645.

Matsuo-Hagiyama, C.; Watanabe, Y.; Tanaka, H.; Takahashi, H.; Arisawa, A.; Yoshioka, E.; Nabatame, S.; Nakano, S. & Tomiyama, N. (2016). Comparison of Silent and Conventional MR Imaging for the Evaluation of Myelination in Children, Magnetic resonance in medical sciences: MRMS: an official journal of Japan Society of Magnetic Resonance in Medicine 16: 209-216. PMID: 27795484.

Hardin, D. P.; Michaels, T. & Saff, E. B. (2016). A Comparison of Popular Point Configurations on S2, Dolomites Research Notes on Approximation, vol. 9., pp. 16-49. PMID: https://arxiv.org/abs/1607.04590.

Gorski, K. M.; Wandelt, B. D.; Hansen, F. K.; Hivon, E. & Banday, A. J. (1999). The HEALPix primer, arXiv:astro-ph/9905275V2. pp. 1-9. PMID: https://arxiv.org/abs/astro-ph/9905275.

Makowski, C.; Lepage, M. & Evans, A. C. (2019). Head motion: the dirty little secret of neuroimaging in psychiatry, Journal of psychiatry & neuroscience, JPN 44: 62-68. PMID: 30565907.

Block, R. I.; Magnotta, V. A.; Bayman, E. O.; Choi, J. Y.; Thomas, J. J. & Kimble, K. K. (2017). Are Anesthesia and Surgery during Infancy Associated with Decreased White Matter Integrity and Volume during Childhood?, Anesthesiology 127: 788-799. PMID: 28837436.

Baud, O. & Saint-Faust, M. (2019). Neuroinflammation in the Developing Brain: Risk Factors, Involvement of Microglial Cells, and Implication for Early Anesthesia, Anesthesia and analgesia 128: 718-725. PMID: 30883417.

Woodward, T. J.; Stamenic, T. T. & Todorovic, S. M. (2019). Neonatal general anesthesia causes lasting alterations in excitatory and inhibitory synaptic transmission in the ventrobasal thalamus of adolescent female rats, Neurobiology of disease, vol. 127, pp. 472-481. PMID: 30825640.

Poddar, S. & Jacob, M. (2016). Dynamic MRI Using Smoothness Regularization on Manifolds (SToRM), IEEE transactions on medical imaging 35: pp. 1-15. PMID: 26685228.

Andre, J. B.; Bresnahan, B. W.; Mossa-Basha, M.; Hoff, M. N.; Smith, C. P.; Anzai, Y. & Cohen, W. A. (2015). Toward Quantifying the Prevalence, Severity, and Cost Associated With Patient Motion During Clinical MR Examinations, Journal of the American College of Radiology, JACR 12: 689-695. PMID: 25963225.

Havsteen, I.; Ohlhues, A.; Madsen, K. H.; Nybing, J. D.; Christensen, H. & Christensen, A. (2017). Are Movement Artifacts in Magnetic Resonance Imaging a Real Problem?—A Narrative Review, frontiers in Neurology 8: 232, pp. 1-8. PMID: 28611728.

Barkovich, M. J.; Xu, D.; Desikan, R. S.; Williams, C. & Barkovich, A. J. (2018). Pediatric neuro MRI: tricks to minimize sedation, Pediatric Radiology 48(1) pp. 50-55. PMID: 28432404.

Brumbaugh, J. E.; Conrad, A. L.; Lee, J. K.; DeVolder, I. J.; Zimmerman, M. B.; Magnotta, V. A.; Axelson, E. D. & Nopoulos, P. C. (2016). Altered brain function, structure, and developmental trajectory in children born late preterm, Pediatric Research, 80: 197-203. PMID: 27064239.

White, T.; Muetzel, R. L.; El Marroun, H.; Blanken, L. M. E.; Jansen, P.; Bolhuis, K.; Kocevska, D.; Mous, S. E.; Mulder, R.; Jaddoe, V. W. V.; van der Lugt, A.; Verhulst, F. C. & Tiemeier, H. (2018). Paediatric population neuroimaging and the Generation R Study: the second wave, European journal of epidemiology 33: pp. 99-125. PMID: 29064008.

Lucinda Q. Uddin & Katherine H. Karlsgodt (2018). Future Directions for Examination of Brain Networks in Neurodevelopmental Disorders, Journal of Clinical Child & Adolescent Psychology, 47:3, 483-497. PMID: 29634380.

Insel, Thomas R. (2007). The arrival of preemptive psychiatry, Early Intervention in Psychiatry 1: 5-6. PMID: 21352102.

Abi-Dargham, A. & Horga, G. (2016). The search for imaging biomarkers in psychiatric disorders, Nature medicine 22: 1248-1255. PMID: 27783066.

APA (2018). Resource Document on Neuroimaging, APA Resource Documents, 112 pgs. PMID: https://www.psychiatry.org/File%20Library/Psychiatrists/Directories/Library-and-Archive/resource_documents/2018-Resource-Neuroimaging.pdf.

Nichols, T. E.; Das, S.; Eickhoff, S. B.; Evans, A. C.; Glatard, T.; Hanke, M.; Kriegeskorte, N.; Milham, M. P.; Poldrack, R. A.; Poline, J.-B.; Proal, E.; Thirion, B.; Van Essen, D. C.; White, T. & Yeo, B. T. T. (2017). Best Practices in Data Analysis and Sharing in Neuroimaging using MRI, Nature neuroscience 20: 299-303. PMID: 28230846.

Uddin, L. Q.; Dajani, D. R.; Voorhies, W.; Bednarz, H. & Kana, R. K. (2017). Progress and roadblocks in the search for brain-based

(56) References Cited

OTHER PUBLICATIONS biomarkers of autism and attention-deficit/hyperactivity disorder, Translational psychiatry 7: e1218. PMID: 28892073.
Bookheimer, S. Y. (2000). Methodological Issues in Pediatric Neuroimaging, Mental Retardation and Developmental Disabilities Research Reviews 6: 161-165. PMID: 10982492.
Greene, D. J.; Black, K. J. & Schlaggar, B. L. (2016). Considerations for MRI Study Design and Implementation in Pediatric and Clinical Populations, Developmental Cognitive Neuroscience 18: 101-112. PMID: 26754461.
Alexander-Bloch, A.; Clasen, L.; Stockman, M.; Ronan, L.; Lalonde, F.; Giedd, J. & Raznahan, A. (2016). Subtle In-Scanner Motion Biases Automated Measurement of Brain Anatomy from in Vivo MRI, Human Brain Mapping 37: 2385-2397. PMID: 27004471.
Pardoe, H. R.; Kucharsky Hiess, R. & Kuzniecky, R. (2016). Motion and morphometry in clinical and nonclinical populations, NeuroImage 135: 177-185. PMID: 27153982.
White, N.; Roddey, C.; Shankaranarayanan, A.; Han, E.; Rettmann, D.; Santos, J.; Kuperman, J. & Dale, A. (2010). PROMO: Real-time Prospective Motion Correction in MRI Using Image-Based Tracking, Magnetic Resonance in Medicine 63: 91-105. PMID: 20027635.
Nielsen, J. A.; Mair, R. W.; Baker, J. T. & Buckner, R. L. (2019). Precision Brain Morphometry: Feasibility and Opportunities of Extreme Rapid Scans, bioRxiv, pp. 1-73. PMID: https://www.biorxiv.org/content/early/2019/01/26/530436.
Madio, D. P. & Lowe, I. J. (1995). Ultra-Fast Imaging Using Low Flip Angles and FIDs, Magn Reson Med 34: 525-529. PMID: 8524019.
Idiyatullin, D.; Corum, C.; Park, J. Y. & Garwood, M. (2006). Fast and quiet MRI using a swept radiofrequency, J Magn Reson 181: 1-8. PMID: 16782371.
Garwood, M. (2013). MRI of fast-relaxing spins, J Magn Reson 229: 49-54. PMID: 23465800.
Gatehouse, P. D. & Bydder, G. M. (2003). Magnetic Resonance Imaging of Short T2 Components in Tissue, Clin Radiol 58: 1-19. PMID: 12565203.
Hagberg, G. E.; Bianciardi, M.; Brainovich, V.; Cassara, A. M. & Maraviglia, B. (2012). Phase stability in fMRI time series: Effect of noise regression, off-resonance correction and spatial filtering techniques, Neuroimage 59: 3748-3761. PMID: 22079450.
Irie, R.; Suzuki, M.; Yamamoto, M.; Takano, N.; Suga, Y.; Hori, M.; Kamagata, K.; Takayama, M.; Yoshida, M.; Sato, S.; Hamasaki, N.; Oishi, H. & Aoki, S. (2014). Assessing Blood Flow in an Intracranial Stent: A Feasibility Study of MR Angiography Using a Silent Scan after Stent-Assisted Coil Embolization for Anterior Circulation Aneurysms, AJNR Am J Neuroradiol, pp. 1-4. PMID: 25523588.
Costagli, M.; Symms, M. R.; Angeli, L.; Kelley, D. A. C.; Biagi, L.; Farnetani, A.; Rua, C.; Donatelli, G.; Tiberi, G.; Tosetti, M. & Cosottini, M. (2015). Assessment of Silent T1-weighted head imaging at 7 T, Eur Radiol 26: 1-10. PMID: 26318369.
Holdsworth, S. J.; Macpherson, S. J.; Yeom, K. W.; Wintermark, M. & Zaharchuk, G. (2018). Clinical Evaluation of Silent T1-Weighted MRI and Silent MR Angiography of the Brain, AJR. American journal of roentgenology 210: 404-411. PMID: 29112472.
Lu, A.; Gorny, K. R. & Ho, M.-L. (2019). Zero TE MRI for Craniofacial Bone Imaging, AJNR. American journal of neuroradiology, 40:(9) pp. 1562-1566. PMID: 31467238.
Baron, C. A.; Dwork, N.; Pauly, J. M. & Nishimura, D. G. (2017). Rapid Compressed Sensing Reconstruction of 3D Non-Cartesian MRI, Magnetic Resonance in Medicine 79: 1-8. PMID: 28940748.
Ohlmann-Knafo, S.; Morlo, M.; Tarnoki, D. L.; Tarnoki, A. D.; Grabowski, B.; Kaspar, M. & Pickuth, D. (2016). Comparison of image quality characteristics on Silent MR versus conventional MR imaging of brain lesions at 3 Tesla, The British Journal of Radiology 89: pp. 1-10. 20150801. PMID: 27626958.
Corum, C. A.; Idiyatullin, D.; Moeller, S. & Garwood, M. (2009). MP-SWIFT with adiabatic inversion preparation for quiet, B1 insensitive T1 weighted imaging, Proc. Intl. Soc. Mag. Reson. Med. 17: 2772. PMID: http://cds.ismrm.org/ protected/09MProceedings/files/02772.pdf.
Chamberlain, R.; Moeller, S.; Corum, C.; Idiyatullin, D. & Garwood, M. (2011). Quiet T1- and T2-weighted brain imaging using SWIFT, Proc. Intl. Soc. Mag. Reson. Med. 19: 2723. PMID: https://archive.ismrm.org/2011/2723.html.
Corum, C. A.; Idiyatullin, D.; Hutter, D.; Everson, L. I.; Eberly, L. E.; Nelson, M. T. & Garwood, M. (2014). DW-MP-Swift for High Spatial Resolution Diffusion Weighted Breast MRI, Proc. Intl. Soc. Mag. Reson. Med. 22: 1054. PMID: https://archive.ismrm.org/2014/1054.html.
Mugler, J. P. & Brookeman, J. R. (1990). Three-dimensional Magnetization-Prepared Rapid Gradient-Echo Imaging (3D MP RAGE), Magn Reson Med 15: 152-157. PMID: 2374495.
Mugler, J. P.; Spraggins, T. A. & Brookeman, J. R. (1991). T2-weighted three-dimensional MP-RAGE MR imaging, J Magn Reson Imaging 1: 731-737. PMID: 1823180.
Calabretta, M. R. & Roukema, B. F. (2007). Mapping on the HEALPix grid, Monthly Notices of the Royal Astronomical Society 381: 865-872. PMID: mnras0381-0865.
Gao, Y.; Du, Z.; Xu, W.; Li, M. & Dong, W. (2019). HEALPix-IA: A Global Registration Algorithm for Initial Alignment, Sensors (Basel, Switzerland) 19: pp. 1-15. PMID: 30669638.
Stehning, C.; Börnert, P.; Nehrke, K.; Eggers, H. & Stuber, M. (2005). Free-Breathing Whole-Heart Coronary MRA with 3D Radial SSFP and Self-Navigated Image Reconstruction, Magn Reson Med 54: 476-480. PMID: 16032682.
Mohsin, Y. Q.; Poddar, S. & Jacob, M. (2019). Free-breathing & ungated cardiac MRI using iterative SToRM (i-SToRM), IEEE transactions on medical imaging. pp. 1-11. PMID: 30932835.
Biswas, S.; Aggarwal, H. K. & Jacob, M. (2019). Dynamic MRI using model-based deep learning and SToRM priors: MoDL-SToRM, Magnetic resonance in medicine 82: 485-494. PMID: 30860286.
Mohsin, Y. Q.; Poddar, S.; Thattayilath, B.; Ansah, D. & Jacob, M. (2018). Navigator-less manifolddata using iterative SToRM, ISMRM, pp. 1-3. PMID: ISMRM2018YM.

* cited by examiner

ROBUST AND COMPUTATIONALLY EFFICIENT MISSING POINT AND PHASE ESTIMATION FOR FID SEQUENCES

CROSS-REFERENCE TO RELATED APPLICATIONS

This Utility Patent Application claims priority under 35 U.S.C. § 371 to International Application No. PCT/US2022/027149, filed Apr. 29, 2022, which claims the benefit of U.S. Provisional Patent Application No. 63/182,658, filed on Apr. 30, 2021 and entitled "ROBUST AND COMPUTATIONALLY EFFICIENT MISSING POINT AND PHASE ESTIMATION FOR FID SEQUENCES", which are incorporated herein by reference.

BACKGROUND

Free induction decay (FID) sequences for magnetic resonance imaging (MRI) such as zero echo time (ZTE) possess many advantages including capturing signals from fast relaxing spins, efficient use of time, and quiet acoustic operation. FID sequences, however, possess one major disadvantage, information from the start of the FID is missing or corrupted due to requirements for radio frequency (RF) pulse time and transmit/receive (T/R) switching (e.g., ZTE) and gradient ramping (e.g., ultrashort echo time (UTE)).

Hybrid methods use separate acquisition of the center of K-space, such as in water- and fat-suppressed proton projection MRI (WASPI) and pointwise encoding time reduction with radial acquisition (PETRA). These methods produce very good results for anatomical scans but limit the ability to acquire dynamic data such as needed for dynamic contrast-enhanced (DCE) scans or motion correction. Methods such as sweep imaging with Fourier transformation (SWIFT) can be used to acquire the center after a small number of acquired views, but are difficult to implement on clinical hardware.

Estimation methods potentially offer the optimum solution to regenerate the missing data in dynamic time series acquisitions but have issues with numeric stability, especially in the presence of phase variation as well as additional modest computation for each view.

For these and other reasons, a need exists for the present invention.

SUMMARY

Disclosed herein is a robust and computationally efficient missing point and phase estimation algorithm originating in the solid state nuclear magnetic resonance (NMR) community for ZTE imaging sequences.

As disclosed herein, a three-dimensional (3D) Radial ZTE sequence was modified to accept table input for view-ordering. All simulated and acquired datasets were reconstructed using 2x oversampled gridding with a radius 4 Kaiser-Bessel kernel and 50 iterations of the Pipe-Menon algorithm for sample density correction. The Pipe-Menon algorithm is described by Pipe, J. G. & Menon, P. *Sampling density compensation in MRI: rationale and an iterative numerical solution.* Magn Reson Med, Department of Radiology, Wayne State University, Detroit, Michigan, USA., Department of Radiology, Wayne State University, Detroit, Michigan, USA., 1999, 41, 179-186, which is incorporated herein by reference. A hollow cube possessing internal slanted sides was simulated by direct synthesis of k-space data and reconstructed by gridding. The modulation transfer function (MTF) in an orthogonal XY slice was estimated with the ImageJ plugin Slanted Edge MTF. ImageJ is a Java-based image processing program developed at the National Institutes of Health and the Laboratory for Optical and Computational Instrumentation (LOCI, University of Wisconsin). Contrast ratio and signal-to-noise ratio (SNR) were evaluated using 32×32 voxel patches in the center slice.

$256^3$ 1 $mm^3$ resolution brain images of a healthy human volunteer were taken using Silent/ZTE using hierarchical equal area isolatitude pixilation of a sphere (HEALPix) view-order with intrinsic T1 weighting, inversion recovery and T2 preparations.

The current disclosure modifies and extends the Stoch/Olejniczak algorithm as disclosed by Stoch, G. and Olejniczak, Z. (2005): *Missing first points and phase artifact mutually entangled in FT NMR data—noniterative solution*, Journal of magnetic resonance (San Diego, Calif.: 1997) 173: 140-152, which is incorporated herein by reference. The distorted FID first has the Nd missing/distorted points set to zero (see FIG. 1A). The distorted projection is generated by fast Fourier transform (FFT) of the distorted FID (see FIG. 1B). The algorithm (described below in the pseudocode) utilizes the Nb point baseline region of the distorted projection, which excludes the region containing object signal, to estimate the missing points. The position of the object is estimated by the magnitude of the distorted spectrum and center between the baseline regions. When the points are correctly estimated this region has minimal real signal. The minimization is accomplished by pseudo inversion of a pre-computed 2*Nd by 2*Nd real matrix, much less numerically onerous than previous methods. Before the missing point estimate, the constant phase is first estimated by an initial deterministic minimization of the real component of the Distorted Projection utilizing multiplication by an Nb by Nb pre-computed complex matrix.

Phase and missing point accuracy, Contrast ratio, MTF performance, and SNR were evaluated before and after correction in the simulated cube object for Nd=0, 1, 2, 3, 4 . . . missing points up until numerical instability (not shown). In-vivo images (see FIGS. 3A-4C) were evaluated for SNR and residual artifactual signal surrounding and contaminating the object (see FIGS. 5A-6A).

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other.

DETAILED DESCRIPTION

Figure 1A:
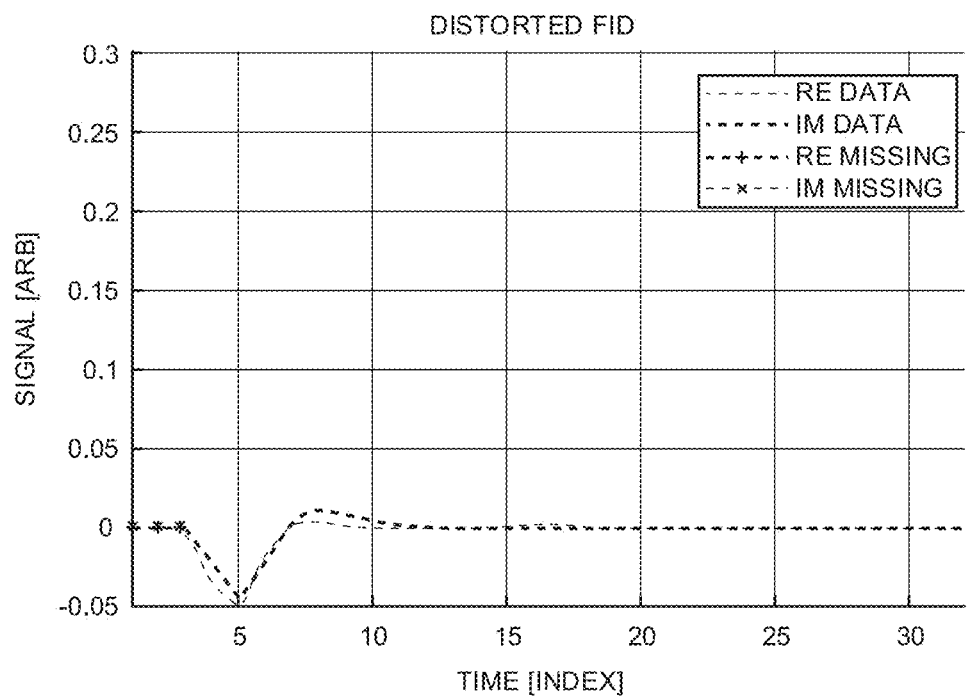
FIG. 1A illustrates one example of a distorted FID.

The emerging set of non-Cartesian free induction decay (FID) imaging sequences offers greatly improved gradient stability, a quiet acoustic environment, and minimal unintended neurostimulation since rapid gradient ramping is not required. These sequences, including zero echo time (ZTE) and sweep imaging with Fourier transformation (SWIFT), are ideal for fast, stable, and repeatable acquisitions while allowing for retrospective motion correction. Advanced reconstruction algorithms work synergistically with these acquisitions, allowing for reduced scan times. Major implementation and standardization barriers prevent the research and clinical communities from utilizing these approaches. Enabling the neuroscience community to rapidly deploy, validate, and translate NGPN is a critical unmet need.

The zero echo time (ZTE) sequence, although not named at the time, was the first MRI method, which utilized hard pulse excitation in a gradient and FID acquisition. It was subsequently re-discovered after Cartesian phase encode echo-based sequences became the norm for MRI.

FID acquisition sequences (SWIFT and ZTE/RUFIS (rotating ultra-fast imaging sequence)) and the similar UTE sequence have been utilized in MRI mainly for musculoskeletal applications. FID acquisition sequences reduce or eliminate the large eddy currents and instabilities many MRI readouts introduce, and also reduce acoustic noise, vibration, and unintended neurostimulation due to drastically reducing gradient slew rates.

While general radial 3D acquisition has been utilized for imaging for some time now in the research community it has found only niche application in research or clinical neuro-imaging, mostly as Silent imaging. One reason has been time consuming reconstruction, which is becoming much less of an issue due to improved algorithms and high performance multi-core personal computers (PCs) and general-purpose graphics processing units GPGPUs.

3D non-Cartesian radial MRI has been an active research topic and niche method for a long time. Reconstruction algorithm efficiency and scanner stability due to gradient drifts, eddy currents and timing errors have limited its usefulness up to now. Until recently, sequences and protocols were not readily available on most clinical scanners. In addition, off-resonance effects at low acquisition bandwidth and gradient non-linearity can limit image quality if not carefully considered or corrected.

Current ZTE acquisitions are limited to low bandwidths (e.g., less than 32 Khz) due to material constraints of coils and switching times of hardware. There are many commercially available head coils on the market for 3T, but most are not capable of FID acquisition sequences, primarily due to long ringdown times. Previous attempts for maximal dampening to reduce the recovery time in coils have been limited to single channel transmit/receive coils or coils for 7T systems, which require local transmit and receive. Another problem for commercially available head coils is that the housing materials produce visible signal, often generating artifacts in the image.

Accordingly, as disclosed herein, 3D radial FID imaging (e.g., ZTE) is utilized with contrast preparations and advanced compressed sensing reconstruction (e.g., smoothness regularization (StoRM) and extensions) for the first time as a silent, motion-correctable, high-stability, high-resolution readout for pediatric neuroimaging. The disclosed 3D radial FID imaging uses an innovative combination, extension, novel application, and optimization of numerous sequences, algorithms, and hardware technologies.

In some embodiments, stable middle to high-bandwidth ZTE acquisition is used with maximal dampening for transmit/receive coils. As disclosed herein, fast transmit/receive capability is added to a pediatric head coil. The FID acquisition coil housing uses new materials and production processes for both FID acquisition and safety (e.g. satisfies UL 94 V/0 and IEC 60601-2-33:2010).

Figure 7A:
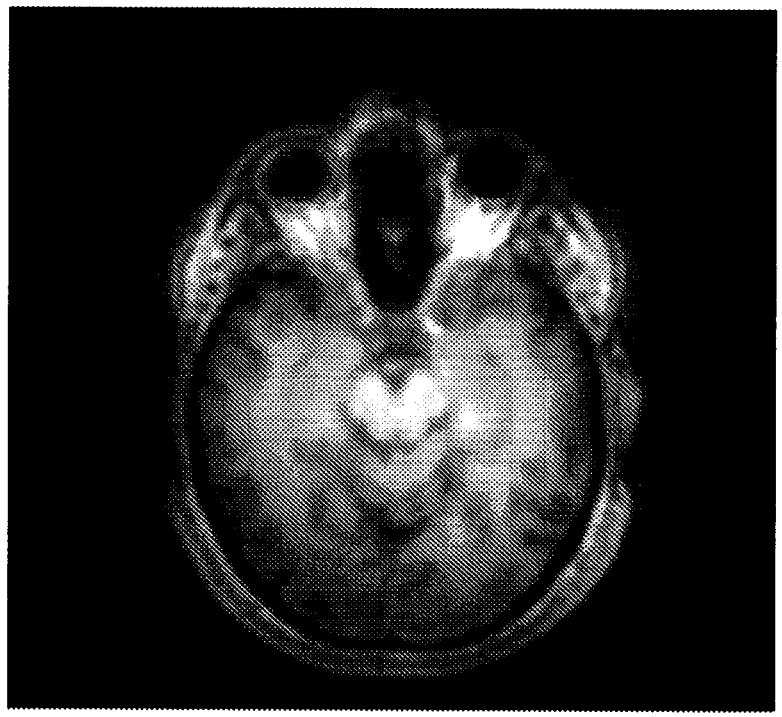
FIGS. 7A and 7B are example preliminary images of a healthy adult male at 3 T using the GE® product "CP" single channel T/R head coil at 32 Khz bandwidth (BW).
Figure 7B:
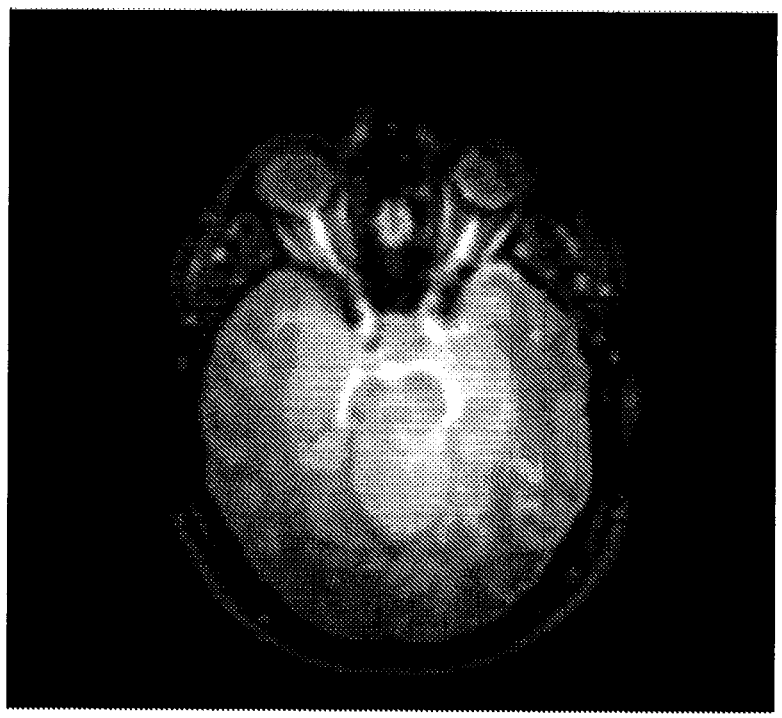

In some embodiments, this disclosure adapts and modifies the ZTE "Silent Scan" sequence available on GE® platforms. As illustrated in FIGS. 7A and 7B, proton density, T1 and T2 images have been acquired with interleaved preparations using a HEALPix view-order on the product single channel transmit receive "CP" coil. FIG. 7A illustrates a T1 prepared ZTE preliminary image of a healthy adult male at 3T using the GE® product "CP" single channel T/R head coil at 32 Khz BW with no intensity flattening or post processing. FIG. 7B illustrates a T2 prepared ZTE preliminary image of a healthy adult male at 3T using the GE® product "CP" single channel T/R head coil at 32 Khz BW with no intensity flattening or post processing. In FIG. 7A, a background signal from coil materials and headphones are visible as background haze. The T2 preparation of FIG. 7B reduces the haze in the image.

Figure 8:
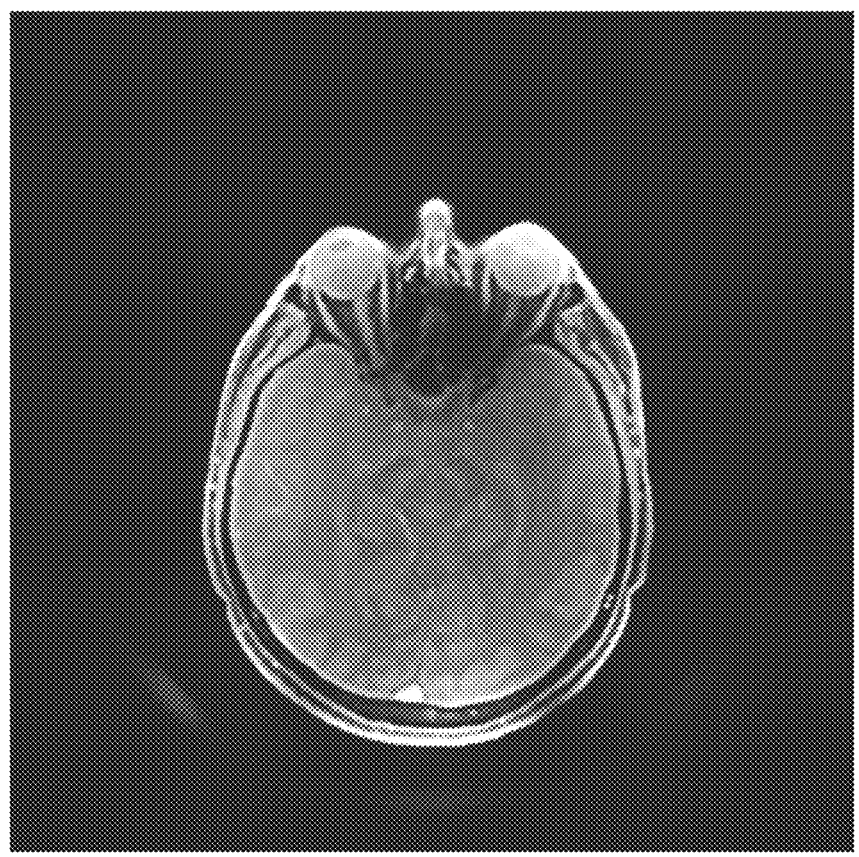
FIG. 8 is an example proton density weighted image of a healthy adult male at 4 T.
Figure 9:
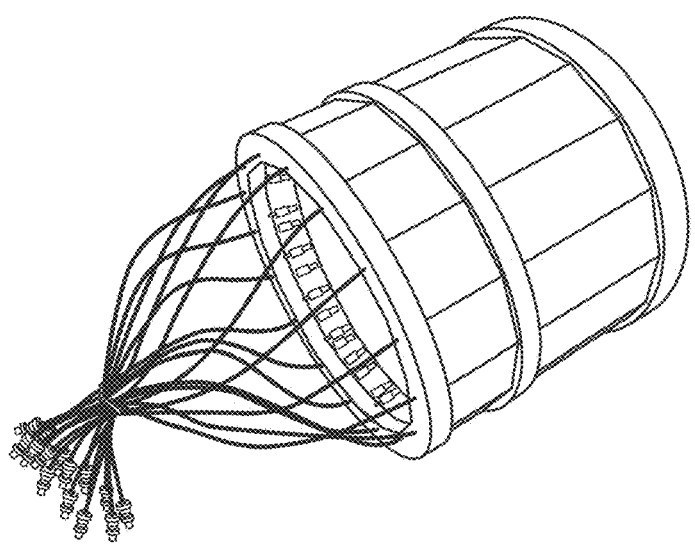
FIG. 9 illustrates an example ZTE/SWIFT-compatible 4 T transceiver head coil.

ZTE-compatible Transceiver Head Coil: FIG. 8 shows a (proton density) PD-weighted SWIFT image of the human head (of a healthy adult male) at 4T collected using a sixteen-channel SWIFT/ZTE compatible transmit/receive microstrip array of a head coil as shown in FIG. 9. The array is housed completely in polytetrafluoroethylene (PTFE) to minimize signal artifacts from the housing.

High Performance T/R switching: In some embodiments, this disclosure uses FID-acquisition sequence-compatible coils and improvements in the receiver chain so that FID acquisition sequences can be run at 32-128 kHz or higher acquisition bandwidths on 3 T MRI systems.

Figure 10:
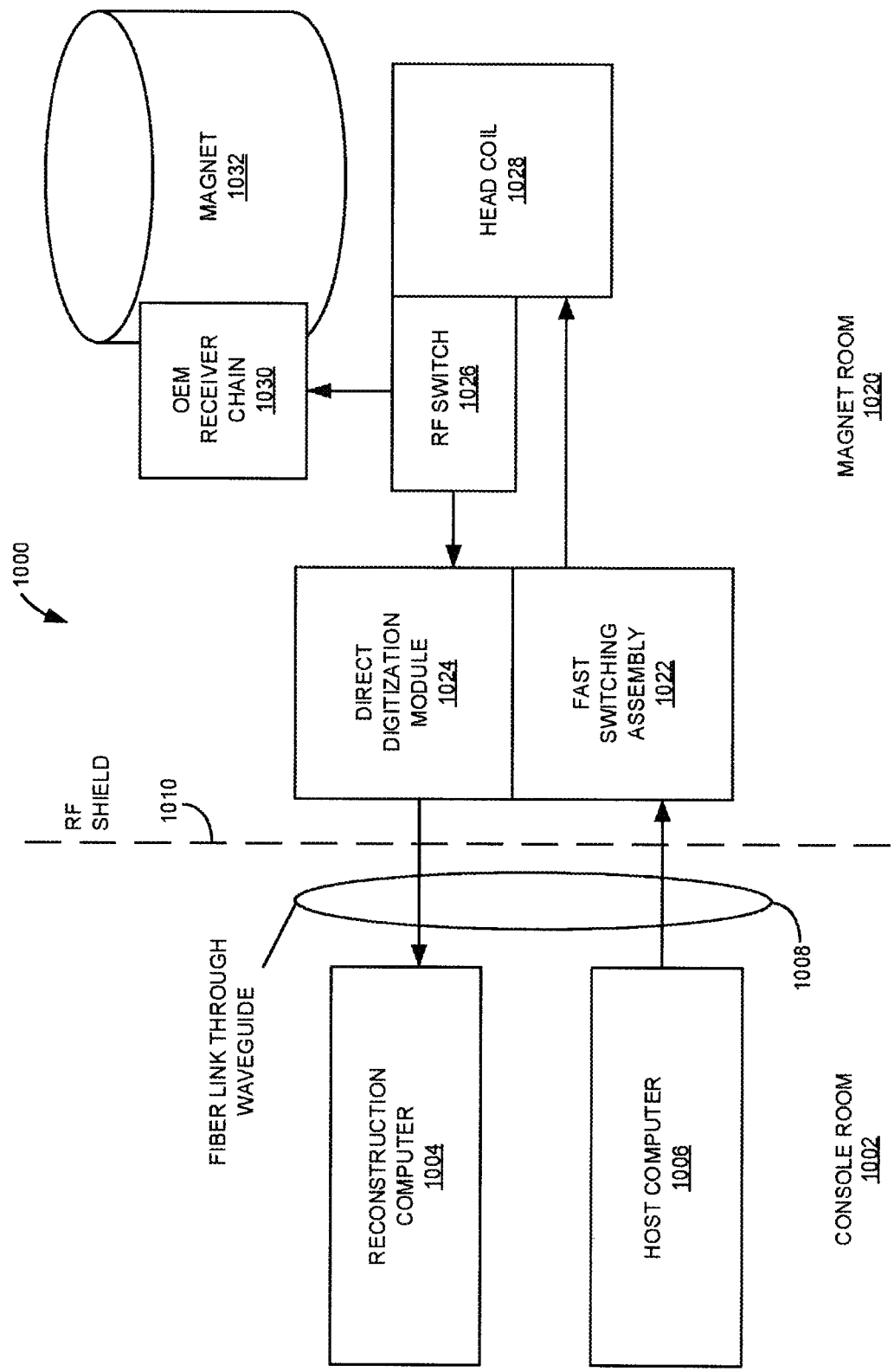
FIG. 10 is a diagram illustrating one example of a next generation pediatric neuroimaging (NGPN) system.

Hardware for high bandwidth (e.g., greater than or equal to 250 kHz) dynamic ZTE acquisition, which is currently unavailable on nearly all OEM systems, is disclosed herein. The block diagram in FIG. 10 shows the components necessary for the NGPN platform.

Because the timing on the parts of the OEM receiver chain is not fast enough to support FID acquisition sequences, additional hardware is used as described below.

Ultra-Fast T/R Switch Assembly: Ultra-fast T/R switches are used to reduce the ringdown time for the transmit coil and preamp protection on the receiver. The assembly may use high-powered PIN diodes, and may allow for ringdown times of less than 1 µs. For the system, in one example, an ultra-fast T/R switch topology may be used similar to the switch topology design described in Brunner, D. O.; Furrer, L.; Weiger, M.; Baumberger, W.; Schmid, T.; Reber, J.; Dietrich, B. E.; Wilm, B. J.; Froidevaux, R. & Pruessmann, K. P. (2016), *Symmetrically biased T/R switches for NMR and MRI with microsecond dead time*, Journal of magnetic resonance (San Diego, Calif.: 1997) 263: 147-155. PMID: 26796113, which is incorporated herein by reference.

Figure 11:
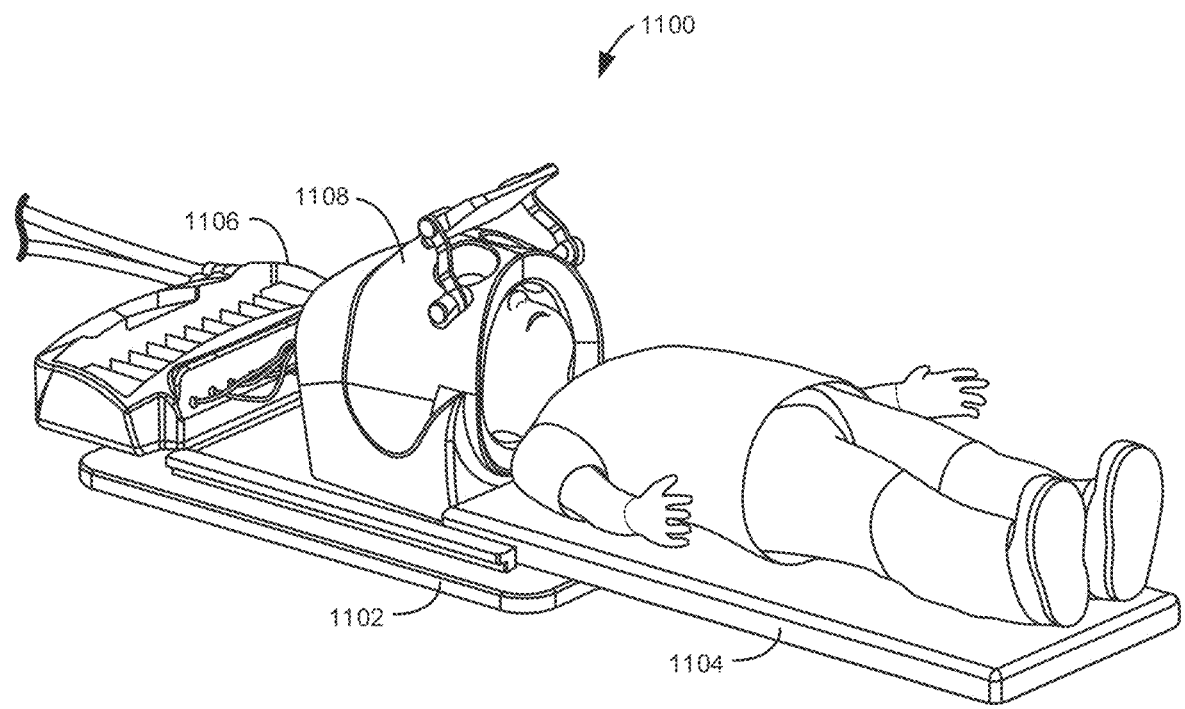
FIG. 11 illustrates one example of a NGPN head coil.

Head Coil: FIG. 11 illustrates one example of a NGPN head coil consisting of a bottom 1102 and slide 1104, preamps and RF switch Assembly 1106, and upper snap on housing 1108 with fMRI window. The design consists of eight overlap decoupled eight transmit/receive loops. This coil is different from commercially available coils in that: (1) all materials inside the coil are free of protons (e.g., PTFE) and (2) additional shielding is requisite to eliminate extraneous signal from the main housing, coil electronics, and the bore liner of the magnet.

In some examples, the head coil may be designed for (1) tune/match, (2) un/loaded Q-ratio, and (3) isolation of transmit and receiver coils (e.g., greater than 50 dB). The T/R switch may be designed for switching times (e.g., ringdown<1 µs). The RF switch may be designed for insertion losses (e.g., IL<0.15 dB) and isolation (e.g., greater than 50 dB). The head coil may also be designed such that the B0 field has no effect. The head coil may be designed to meet clinically acceptable SNR (e.g., National Electrical Manufacturers Association (NEMA) 1, 3, and 9) with no visible signal from the housing materials.

FIG. 1A illustrates one example of a distorted FID. FIG. 1A includes the signal versus time for real (RE) data and imaginary (IM) data including the real missing (or corrupted) points and the imaginary missing (or corrupted) points.

Figure 1B:
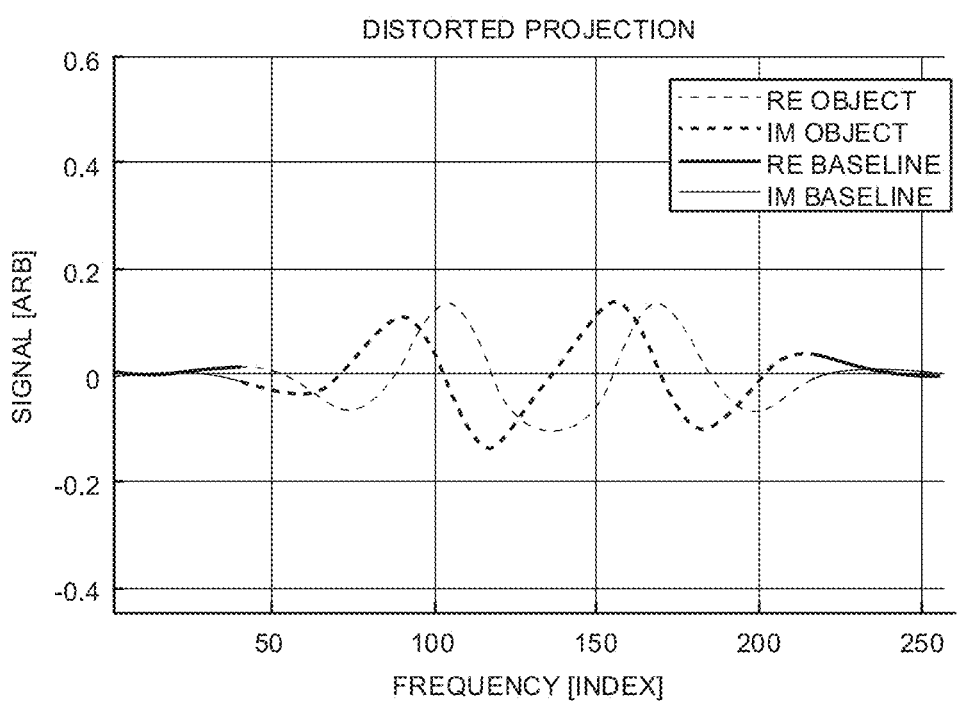
FIG. 1B illustrates one example of a distorted projection.

FIG. 1B illustrates one example of a distorted projection corresponding to the distorted FID of FIG. 1A. FIG. 1B includes the signal versus frequency for the real object and the imaginary object including the real baseline and the imaginary baseline.

Figure 2A:
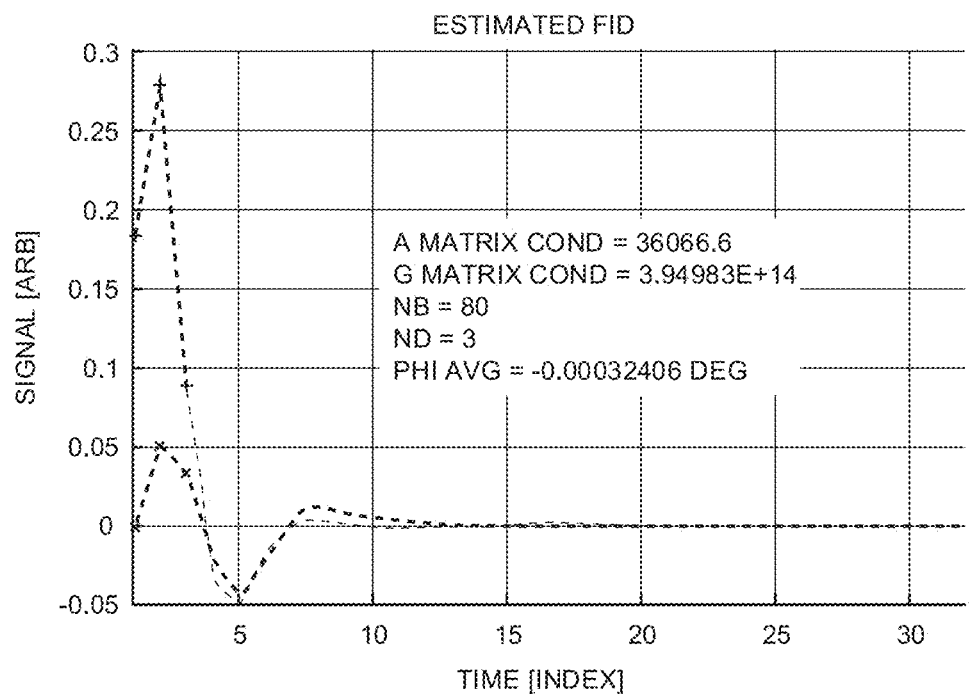
FIG. 2A illustrates one example of a corrected FID.

FIG. 2A illustrates one example of a corrected FID. FIG. 2A includes the signal versus time for real data and imaginary data including estimated real points for the real missing (or corrupted) points and estimated imaginary points for the imaginary missing (or corrupted) points.

Figure 2B:
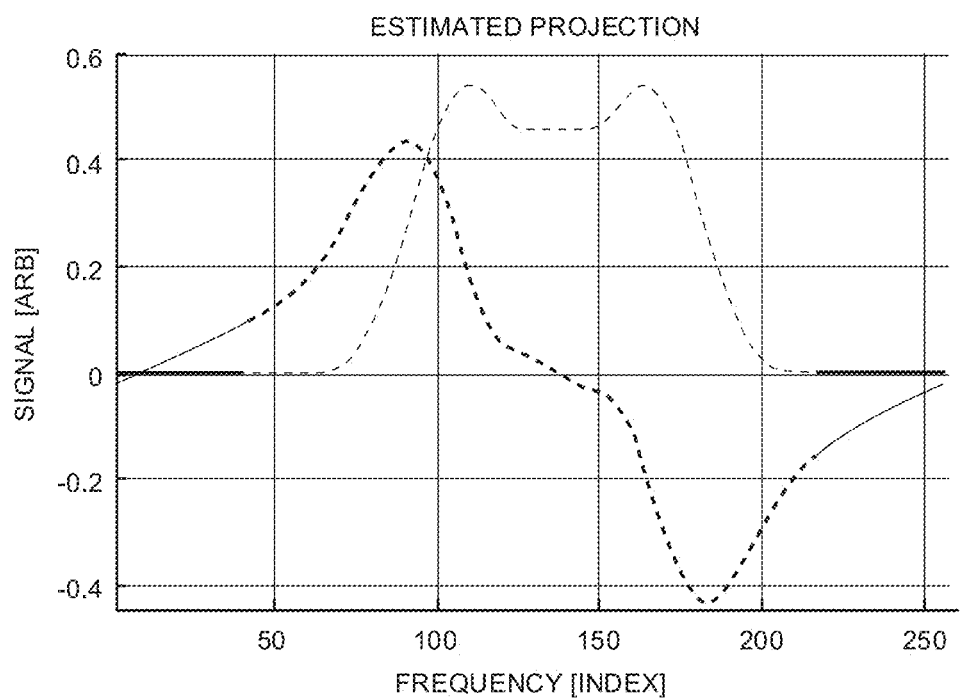
FIG. 2B illustrates one example of a corrected projection.
Figure 4A:
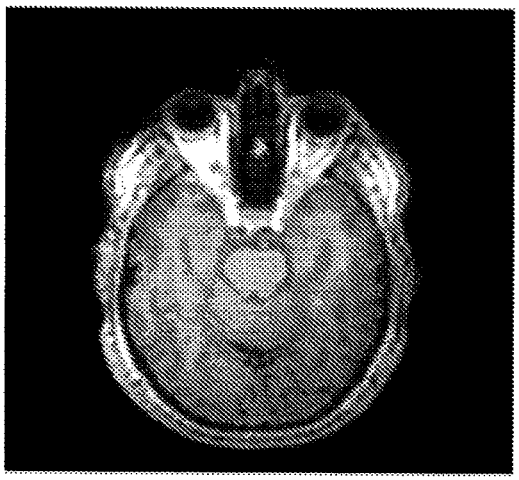
FIGS. 3A-4C are example brain images of a healthy adult subject.

FIG. 2B illustrates one example of a corrected projection corresponding to the corrected FID of FIG. 2A. FIG. 2B includes the signal versus frequency for the real object and the imaginary object including the real baseline and the imaginary baseline.

Figure 3A:
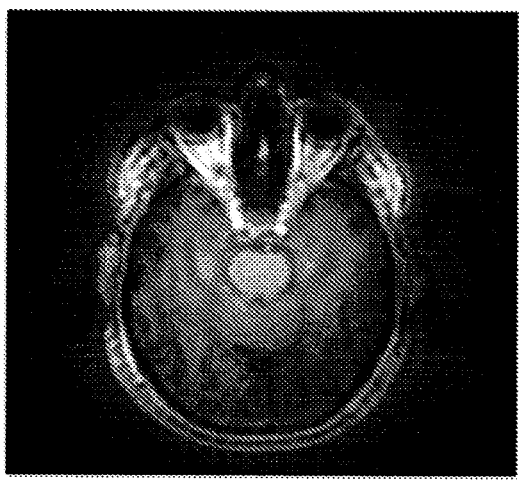
Figure 4B:
Figure 3B:
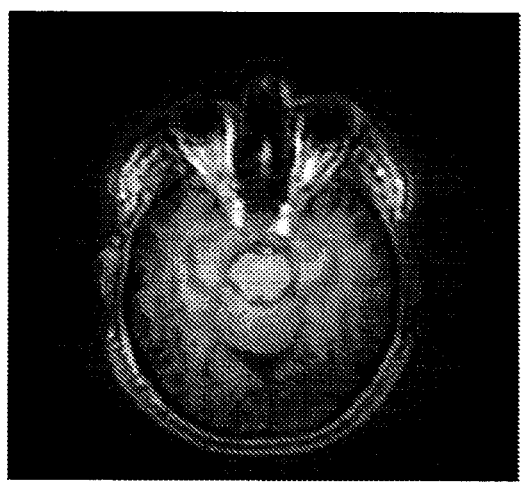
Figure 4C:
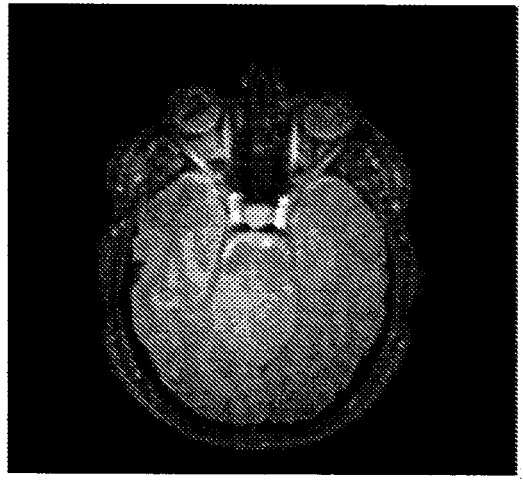
Figure 3C:
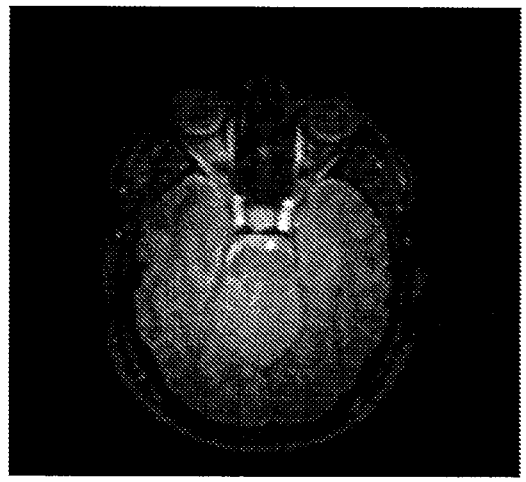

FIGS. 3A-4C are example brain images of a healthy adult subject. FIG. 3A illustrates an un-corrected ZTE intrinsic contrast image. FIG. 3B illustrates an IR-ZTE image. FIG. 3C illustrates a T-ZTE image. FIG. 4A illustrates a corrected (Nd=3) ZTE intrinsic contrast image. FIG. 4B illustrates an IR-ZTE image. FIG. 4C illustrates a T-ZTE image.

Figure 6C:
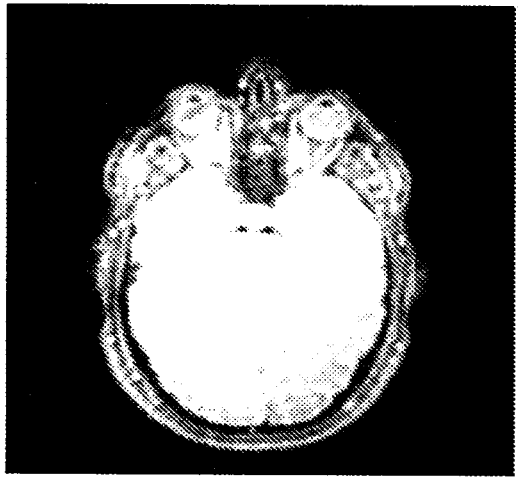
FIGS. 5A-6C are other example brain images of a healthy adult subject.
Figure 5C:
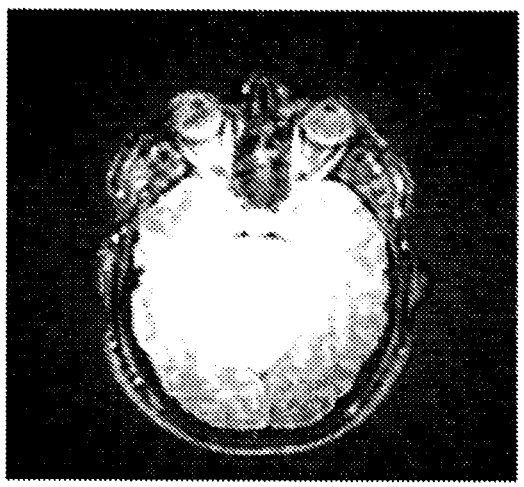
Figure 6B:
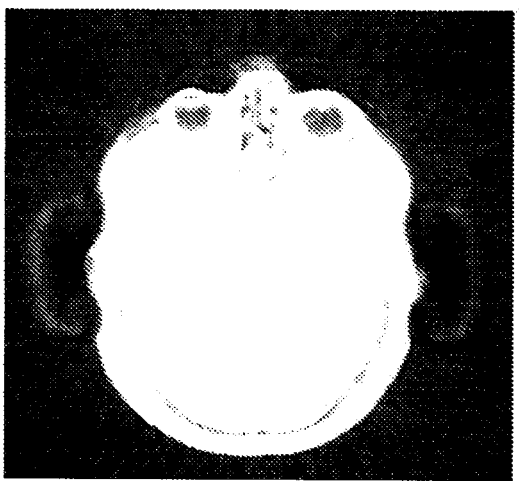
Figure 5B:
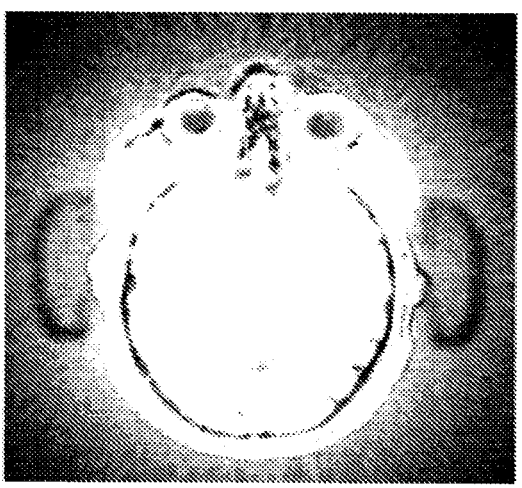
Figure 6A:
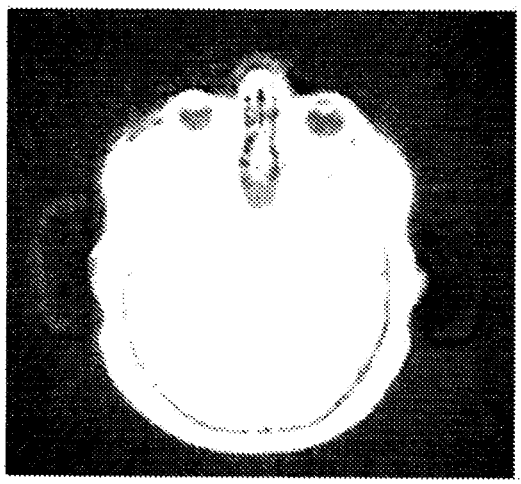
Figure 5A:
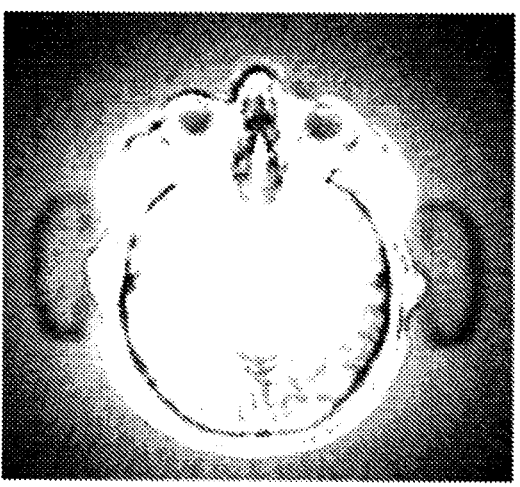

FIGS. 5A-6C are other example brain images of a healthy adult subject. For FIGS. 5A-6C, the intensity scale is set to 5× showing removal of in and out of object artefactual signal. FIG. 5A illustrates an un-corrected ZTE intrinsic contrast image. FIG. 5B illustrates an IR-ZTE image. FIG. 5C illustrates a T-ZTE image. FIG. 6A illustrates a corrected (Nd=3) ZTE intrinsic contrast image. FIG. 6B illustrates an IR-ZTE image. FIG. 6C illustrates a T2-ZTE image.

FIGS. 7A and 7B are example preliminary images of a healthy adult male at 3 T using the GE® product "CP" single channel T/R head coil at 32 Khz bandwidth (BW). For FIGS. 7A and 7B, no intensity flattening or post processing was used. FIG. 7A illustrates a T1 prepared ZTE image. FIG. 7B illustrates a T2 prepared ZTE image. In FIG. 7A, a background signal from coil materials and headphones are visible as background haze. The T2 preparation of FIG. 7B reduces the haze in the image.

FIG. 8 is an example proton density weighted image of a healthy adult male at 4 T. Signal from padding can be seen as bright bars next to the coil elements.

FIG. 9 illustrates an example ZTE/SWIFT-compatible 4 T Transceiver Head Coil. In some examples the head coil has 8/16 channels.

FIG. 10 is a diagram illustrating one example of a next generation pediatric neuroimaging (NGPN) system 1000. System 1000 includes a console room 1002 and a magnet room 1020. The console room 1002 is separated from the console room 1020 by an RF shield 1010. A host computer 1006 and a reconstruction computer 1004 are located in the console room 1002. A fast switching assembly 1022, a direct digitization module 1024, an RF switch 1026, a head coil 1028, an OEM receiver chain 1030, and a magnet 1032 are located in the magnet room 1020.

The host computer 1006 is communicatively coupled to the fast switching assembly 1022 through a fiber link through waveguide 1008. The reconstruction computer 1004 is communicatively coupled to the direct digitization module 1024 through the fiber link through waveguide 1008. The fast switching assembly 1022 is electrically coupled to the head coil 1028. The head coil 1028 is electrically coupled to the RF switch 1026. The RF switch 1026 is electrically coupled to the direct digitization module 1024 and the OEM receiver chain 1030. The OEM receiver chain 1030 is electrically coupled to the magnet 1032.

Host computer 1006 controls the operation of fast switching assembly 1022 to acquire MRI data of a patient. Host computer 1006 may include any suitable processing system. Head coil 1028 includes a transmit coil and a receiver coil. A proton free polymer housing may enclose the transmit coil and the receiver coil. Fast switching assembly 1022 controls the transmit coil. The receiver coil is responsible for signal reception. RF switch 1026 may pass the analog data from the receiver coil to the OEM receiver chain 1030 or to direct digitization module 1024. Direct digitization module 1024 converts the analog data to digital data and passes the digital data to reconstruction computer 1004. The reconstruction computer 1004 may be any device that can read in the digitized data and process the data in accordance with the missing point and phase estimation for FID sequences algorithm. In some examples, the reconstruction computer 1004 is a desktop workstation/computer. In other examples, the reconstruction computer 1004 may be part of the host computer 1006. In yet other examples, the reconstruction computer 1004 may be part of a cloud computing system, a dedicated server, a desktop workstation/computer, a mobile device, or another suitable open/closed source hardware and software system capable of processing the digitized data.

FIG. 11 illustrates one example of a NGPN head coil 1100. Head coil 1100 includes a bottom 1102 and slide 1104, preamps and RF switch assembly 1106, and an upper snap on housing 1108 with fMRI window.

Figure 12:
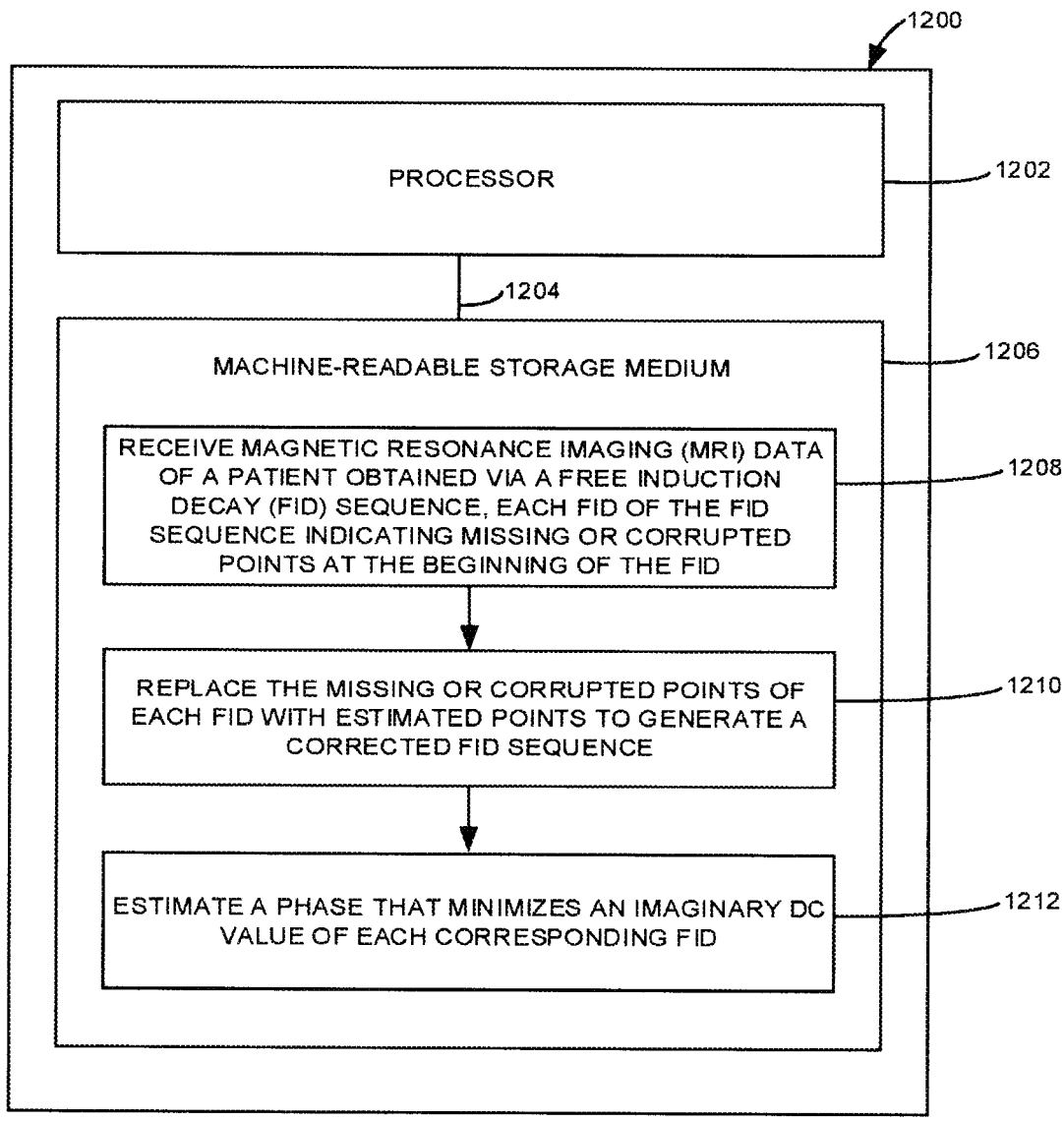
FIG. 12 illustrates one example of a processing system for implementing missing point and phase estimation for FID sequences.

FIG. 12 illustrates one example of a processing system 1200 for implementing missing point and phase estimation for FID sequences. In one example, system 1200 provides reconstruction computer 1004 previously described and illustrated with reference to FIG. 10. System 1200 includes a processor 1202 and a machine-readable storage medium 1206. Processor 1202 is communicatively coupled to machine-readable storage medium 1206 through a communication path 1204. Although the following description refers to a single processor and a single machine-readable storage medium, the description may also apply to a system with multiple processors and multiple machine-readable storage mediums. In such examples, the instructions may be distributed (e.g., stored) across multiple machine-readable storage mediums and the instructions may be distributed (e.g., executed by) across multiple processors.

Processor 1202 includes one (i.e., a single) central processing unit (CPU) or microprocessor or graphics processing unit (GPU) or more than one (i.e., multiple) CPU or microprocessor or GPU, and/or other suitable hardware devices for retrieval and execution of instructions stored in machine-readable storage medium 1206. Processor 1202 may fetch, decode, and execute instructions 1208-1212 to perform missing point and phase estimation for FID sequences.

Processor 1202 may fetch, decode, and execute instructions 1208 to receive magnetic resonance imaging (MRI) data of a patient obtained via a free induction decay (FID) sequence, each FID of the FID sequence indicating missing or corrupted points at the beginning of the FID. In one example, the FID sequence comprises a sweep imaging with Fourier transformation (SWIFT) sequence or a zero echo time (ZTE) sequence. The bandwidth of the ZTE sequence may be greater than or equal to 62.5 kHz.

Processor 1202 may fetch, decode, and execute instructions 1210 to replace the missing or corrupted points of each FID with estimated points to generate a corrected FID sequence. In one example, the processor 1202 executes the instructions to replace the missing or corrupted point by an estimate from the uncorrupted points.

Processor 1202 may fetch, decode, and execute instructions 1212 to estimate a phase that minimizes an imaginary DC value of each corresponding FID. In one example, the processor 1202 executes the instructions to estimate the phase by minimizing a magnitude of a baseline region in a projection.

As an alternative or in addition to retrieving and executing instructions, processor 1202 may include one (i.e., a single) electronic circuit or more than one (i.e., multiple) electronic circuit comprising a number of electronic components for performing the functionality of one of the instructions or more than one of the instructions in machine-readable storage medium 1206. With respect to the executable instruction representations (e.g., boxes) described and illustrated herein, it should be understood that part or all of the executable instructions and/or electronic circuits included within one box may, in alternate examples, be included in a different box illustrated in the figures or in a different box not shown.

Machine-readable storage medium 1206 is a non-transitory storage medium and may be any suitable electronic, magnetic, optical, or other physical storage device that stores executable instructions. Thus, machine-readable storage medium 1206 may be, for example, random access memory (RAM), electrically erasable programmable read-only memory (EEPROM), a storage drive, an optical disc, and the like. Machine-readable storage medium 1206 may be disposed within system 1200, as illustrated in FIG. 12. In this case, the executable instructions may be installed on system 1200. Alternatively, machine-readable storage medium 1206 may be a portable, external, or remote storage medium that allows system 1200 to download the instructions from the portable/external/remote storage medium. In this case, the executable instructions may be part of an installation package.

Figure 13:
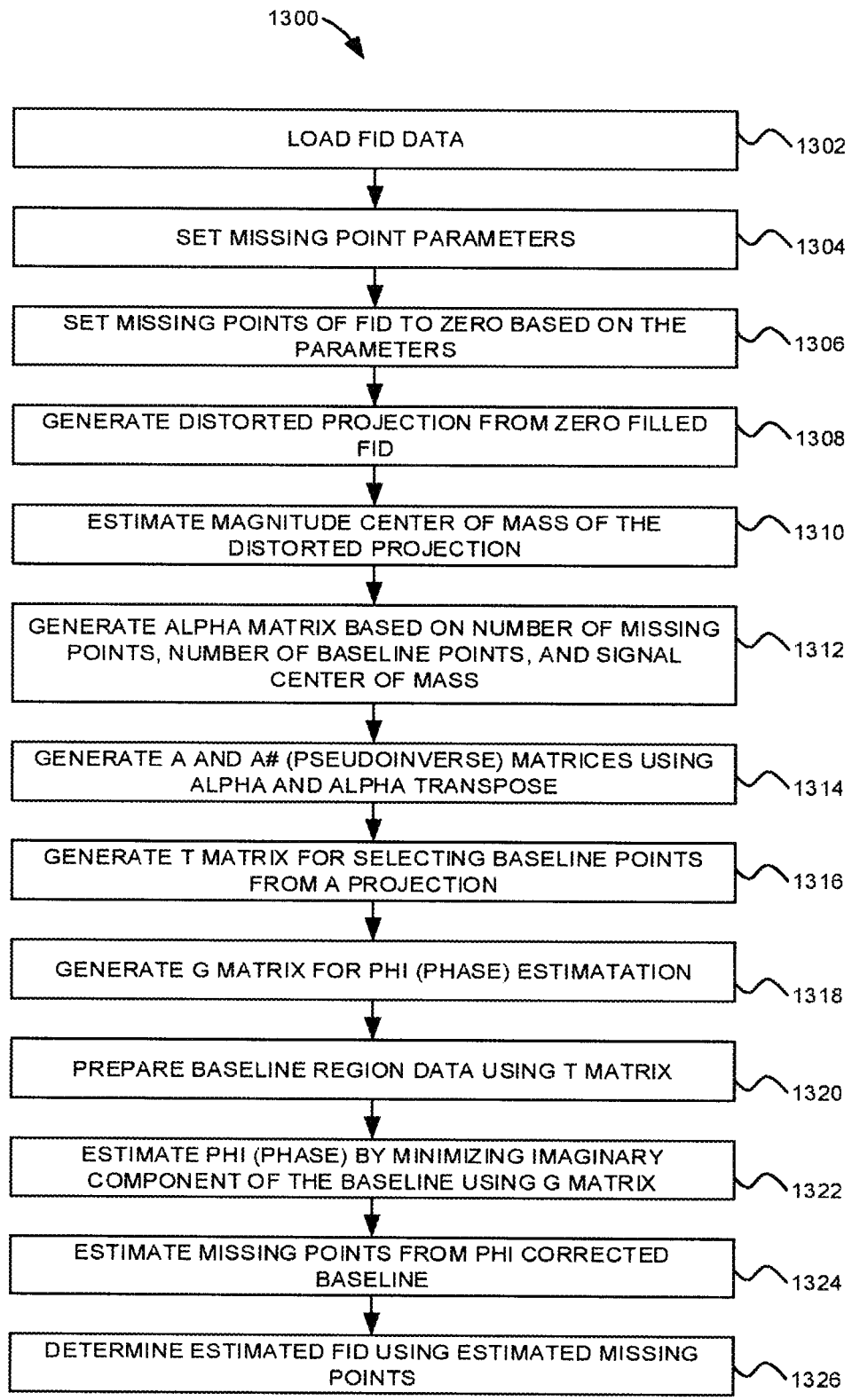
FIG. 13 is a flow diagram illustrating one example of a method for performing missing point and phase estimation for FID sequences.

FIG. 13 is a flow diagram illustrating one example of a method 1300 for performing missing point and phase estimation for FID sequences. In some examples, method 1300 may be implemented by processing system 1200 of FIG. 12 or reconstruction computer 1004 of FIG. 10. At 1302, method 1300 includes loading FID data. The data includes a FID sequence including missing or corrupted points. At 1304, method 1300 includes setting missing point parameters. The parameters include the number of FID points to use (N), the missing points (Nd), and the baseline points (Nb). At 1306, method 1300 includes setting the missing points of the FID to zero based on the parameters. At 1308, method 1300 includes generating a distorted projection from the zero filled FID. At 1310, method 1300 includes estimating a magnitude of the center of mass of the distorted projection. At 1312, method 1300 includes generating an alpha matrix based on the number of missing points, the number of baseline points, and the signal center of mass. At 1314, method 1300 includes generating A and A # (pseudo-inverse) matrices using alpha and alpha transpose. At 1316, method 1300 includes generating a T matrix for selecting baseline points from a projection. At 1318, method 1300 includes generating a G matrix for phi (phase) estimation. At 1320, method 1300 includes preparing baseline region data using the T matrix. At 1322, method 1300 includes estimating phi (phase) by minimizing the imaginary component of the baseline using the G matrix. At 1324, method 1300 includes estimating missing points from the phi corrected baseline. At 1326, method 1300 includes determining an estimated FID using the estimated missing points. The method includes looping through each channel and view direction in the data.

The following pseudocode, with reference to example data and figures, describes one example of an algorithm that may be executed to implement the method 1300 of FIG. 13 including missing point and phase estimation for FID sequences.

Pseudocode 0.1 Load Simulated or Actual Data (e.g., 1302 of FIG. 13)

Example

/home/curt/src/ngfn_recon_uiowa_clean/matlab/vieworders/silent_grad_25_recon_noise0_0mp_20220422T153702/forSSN_3d_silent_grad_25.txt.mat

```
dict_keys(['D', 'D1', 'Df', 'Df_1', 'L', 'L1', 'R', 'R1',
    'T2', 'T2_1', 'TA', 'TA_1', 'csm', 'csm_size', 'dcf',
    'dcf_size', 'fname', 'kdata', 'kdata_size', 'knav',
    'knav_size', 'ktraj', 'ktraj_nav', 'ktraj_nav_size',
    'ktraj_size', 'rp', 'rp_1'])
k-space array shape: (128, 192, 64, 8)
coordinate array shape: (3, 128, 192, 64)
dcf array shape: (128, 192, 64)
New k-space array shape: (8, 128, 192, 64)
New coordinate array shape: (128, 192, 64, 3)
128.0
0.90235937
[1]: ## Shapes
Nc=ksp.shape[0] # channels
N=ksp.shape[1] # fid length
Nv=ksp.shape[2] # views per segment
Ns=ksp.shape[3] # segments
total_views=Nv*Ns*Nc
print('Nc=', Nc)
print('N=', N)
print('Nv=', Nv)
print('Ns=', Ns)
print('total_views=', total_views)
```

Example

```
Nc=8
N=128
Nv=192
Ns=64
total_views=98304
```

0.2 Missing Point Parameters (e.g., 1304 of FIG. 13)

N is the number of points in the FID. Nd is the number of missing or 'distorted' points that need to be estimated at the beginning. Nb is the number of baseline points to use. This example shows a small length FID but the method works with longer lengths.

```
[2]: # Number of FID Points to Use, Missing Points,
Baseline Points
    N=32
    Nd=2
    Nb=int(N*7/16)
    N_show=32
    center_proj=True
    apply_phi=True
    print('N=', N)
    print('Nd=', Nd)
    print('Nb=', Nb)
```

Example

```
N=32
Nd=2
Nb=14
```

0.3 True FID, No Missing or Distorted Points

This is a case where the missing points are known from simulation, to test the accuracy of the method. An arbitrary constant phase, typical of MRI channels due to propagation delays is applied.

```
[3]: phi_true_deg=45.0
    phi_true=phi_true_deg*pi/180
```

```
    fid_true=ksp[0, 0:N, 0, 0] # loop through all FIDs in the
        dataset
    fid_true=fid_true*np.exp(1j*phi_true) # phase for testing
[4]: plt.figure(clear=True)
    plt.title('True FID')
    plt.plot(fid_true.real[0:N_show], label='Real')
    plt.plot(fid_true.imag[0:N_show], label='Imag')
    plt.xlabel('Time Index')
    plt.ylabel('Signal [arb]')
    plt.legend( )
    plt.show( )
```

Example

Figure 14A:
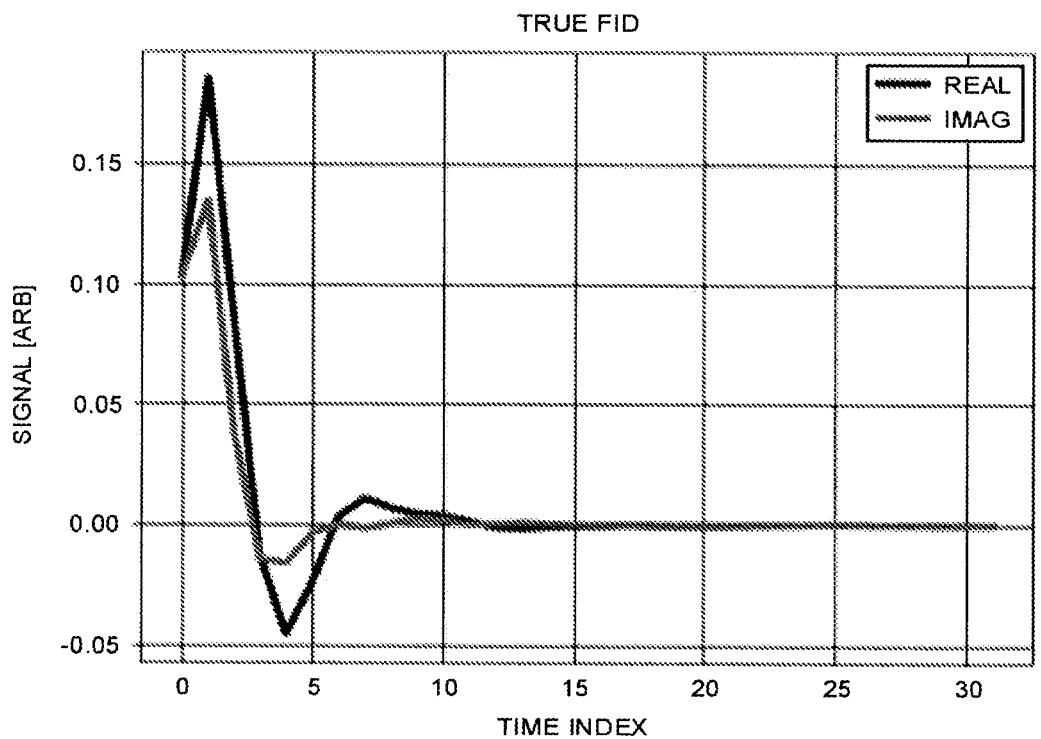
FIG. 14A illustrates one example of a true FID with no missing or distorted points.

FIG. 14A illustrates one example of a true FID with no missing or distorted points.

FIG. 14A includes the signal versus time for the real object and the imaginary object.

0.4 True Projection, From True FID

```
[5]: # True Projection
    p_true=fft.fftshift(fft.fft(fid_true))
[6]: plt.figure(clear=True)
    plt.title('True Projection')
    plt.plot(p_true.real, label='Real')
    plt.plot(p_true.imag, label='Imag')
    plt.xlabel('Frequency Index')
    plt.ylabel('Signal [arb]')
    plt.legend( )
    plt.show( )
```

Example

Figure 14B:
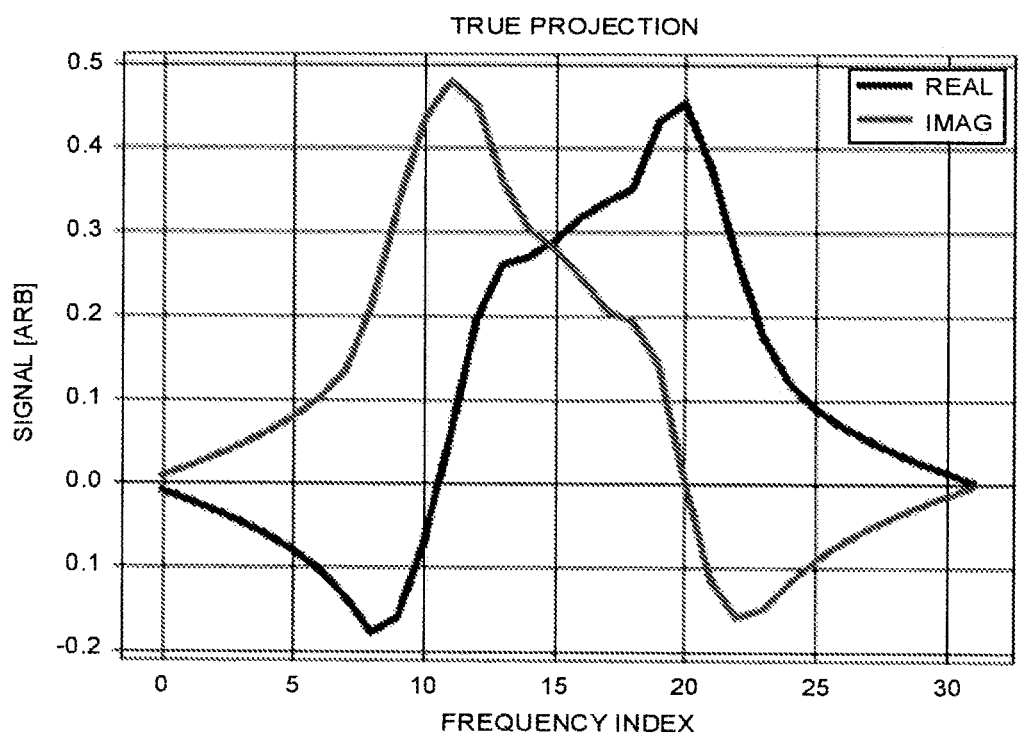
FIG. 14B illustrates one example of a true projection from the true FID of FIG. 14A.

FIG. 14B illustrates one example of a true projection from the true FID of FIG. 14A.

FIG. 14B includes signal versus frequency for the real object and the imaginary object.

0.5 FID With Missing or Distorted Points Set to Zero (e.g., 1306 of FIG. 13)

The number of corrupted complex data points, known from timing parameters, are set. These are set to zero. If the FID consists of the corrupted points already trimmed from the beginning, the number of missing points, values set to zero are pre-pended to the FID.

```
[7]: # Distorted (Corrupted Points Zeroed) FID, and
Arbitrary Phase
    fid_dist=fid_true.copy( ) # just first fid for now
    fid_dist[0:Nd]=0.0+1j*0.0
[8]: plt.figure(clear=True)
    plt.title('Zeroed FID')
    plt.plot(fid_dist.real[0:N_show], label='Real')
    plt.plot(fid_dist.imag[0:N_show], label='Imag')
    plt.xlabel('Time Index')
    plt.ylabel('Signal [arb]')
    plt.legend( )
    plt.show( )
```

Example

Figure 14C:
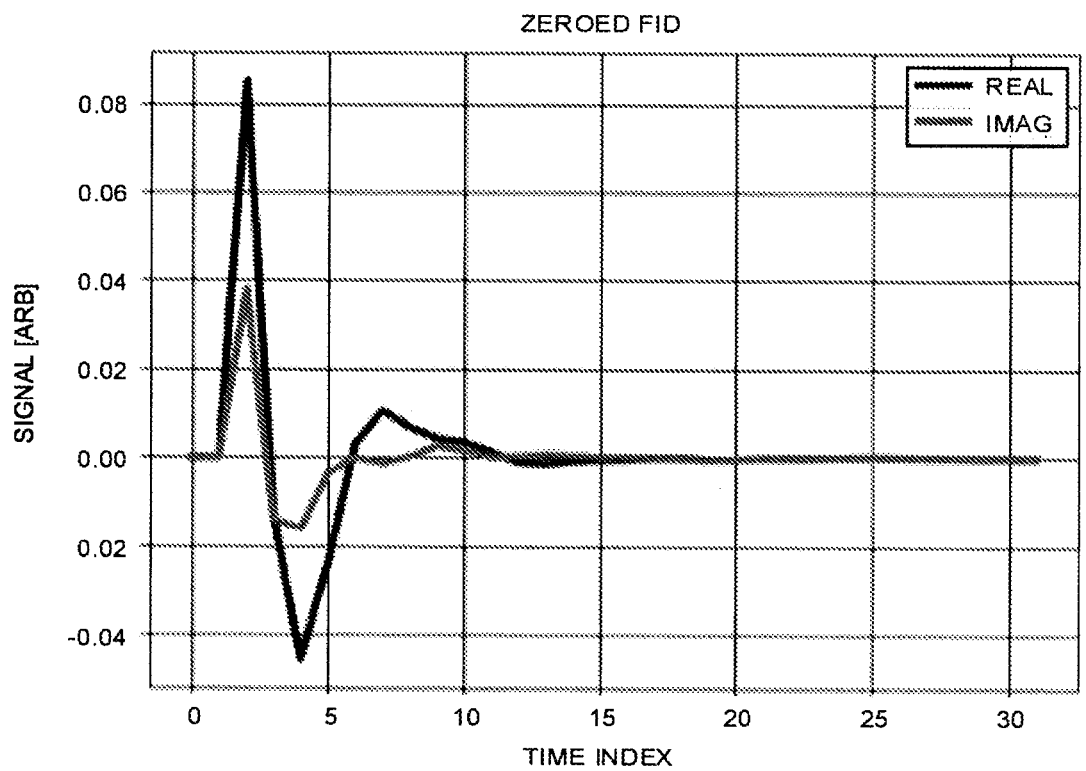
FIG. 14C illustrates one example of a FID with missing or distorted points set to zero.

FIG. 14C illustrates one example of a FID with missing or distorted points set to zero. FIG. 14C includes signal versus time for the real object and the imaginary object.

0.6 Projection From Zero Filled FID (e.g., 1308 of FIG. 13)

The distorted projection is generated by Fourier transformation.
[9]: # Distorted Projection
p_dist=fft.fftshift(fft.fft(fid_dist))
[10]: plt.figure(clear=True)
plt.title('Distorted Projection')
plt.plot(p_dist.real, label='Real')
plt.plot(p_dist.imag, label='Imag')
plt.xlabel('Frequency Index')
plt.ylabel('Signal [arb]')
plt.legend( )
plt.show( )

Example

Figure 14D:
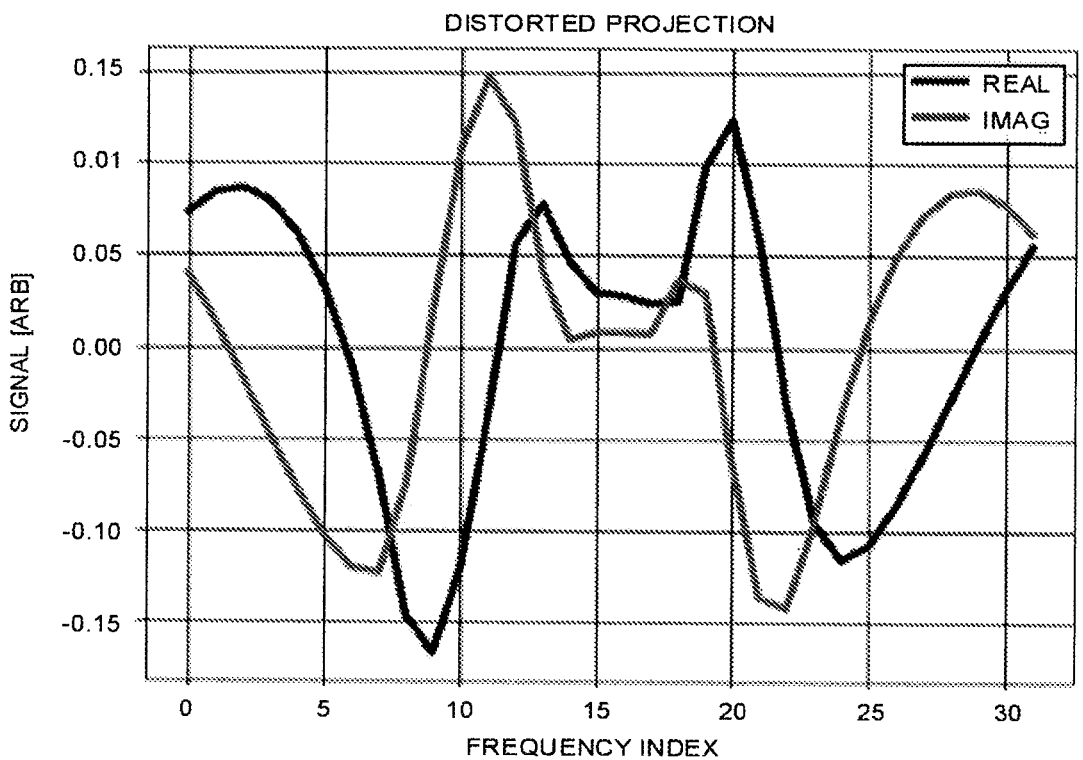
FIG. 14D illustrates one example of a distorted projection from the zero filled FID of FIG. 14C.

FIG. 14D illustrates one example of a distorted projection from the zero filled FID of FIG. 14C. FIG. 14D includes the signal versus frequency for the real object and the imaginary object.

0.7 Estimate Magnitude Center of Mass of the Distorted Projection (e.g., 1310 of FIG. 13)

The center of mass of the magnitude signal is used as an estimate of the location of the object.
[11]: # Find Magnitude Centroid and Shift
if center_proj:
    p_com=np.arange(N)@np.abs(p_dist)/np.sum(np.abs (p_dist))
    p_com_shift=int(np.round(p_com-(N/2-1)))
    p_dist=np.roll(p_dist, -p_com_shift)
    fid_dist=fft.ifft(fft.ifftshift(p_dist))
else:
    p_com_shift=0
print('p_com_shift=', p_com_shift)

Example p_com_shift=0

0.8 Alpha (e.g., 1312 of FIG. 13)

The alpha matrix is precomputed based on the number of missing points, the number of baseline points, and the signal center of mass. The rows of alpha are the Fourier basis functions corresponding to each component (real or imaginary) of a missing point. Even column indices correspond to real values in the complex FID, odd indices the imaginary component.
[12]: # Hybrid Vector Representing Nb Real and Nd Complex Values
alpha=np.zeros((Nb, 2*Nd))
[13]: const=2*pi/N
zero_f_idx=int(N/2)
nu_idxs=np.arange(N)-zero_f_idx
[14]: Assert nu_idxs[zero_f_idx]==0
[15]: # Identifies Indices of Usable Baseline
nu_idxs_shift=int(Nb/2-round(zero_f_idx-(N/2)))
nu_idxs=np.roll(nu_idxs, nu_idxs_shift)
nu_idxs=nu_idxs[:Nb]
[16]: print(nu_idxs)

Example

[9 10 11 12 13 14 15 −16 −15 −14 −13 −12 −11 −10]
[17]: For idx in Range(2*Nd):
m_idx=int(idx/2);
coson_switch_n=(idx+1)% 2; sinon_switch_n= 1-coson_switch_n;
alpha[:, idx]=coson_switch_n*np.cos (const*m_idx*nu_idxs)+ ↵ sinon_switch_n*np.sin (const*m_idx*nu_idxs)
[18]: label_vec=['0', '1', '2', '3', '4', '5', '6', '7', '8', '9']
plt.figure( )
plt.title('alpha columns')
plt.plot(alpha, label=label_vec[:2*Nd])
plt.xlabel('Row Index')
plt.ylabel('Value')
plt.legend( )
plt.show( )

Example

Figure 14E:
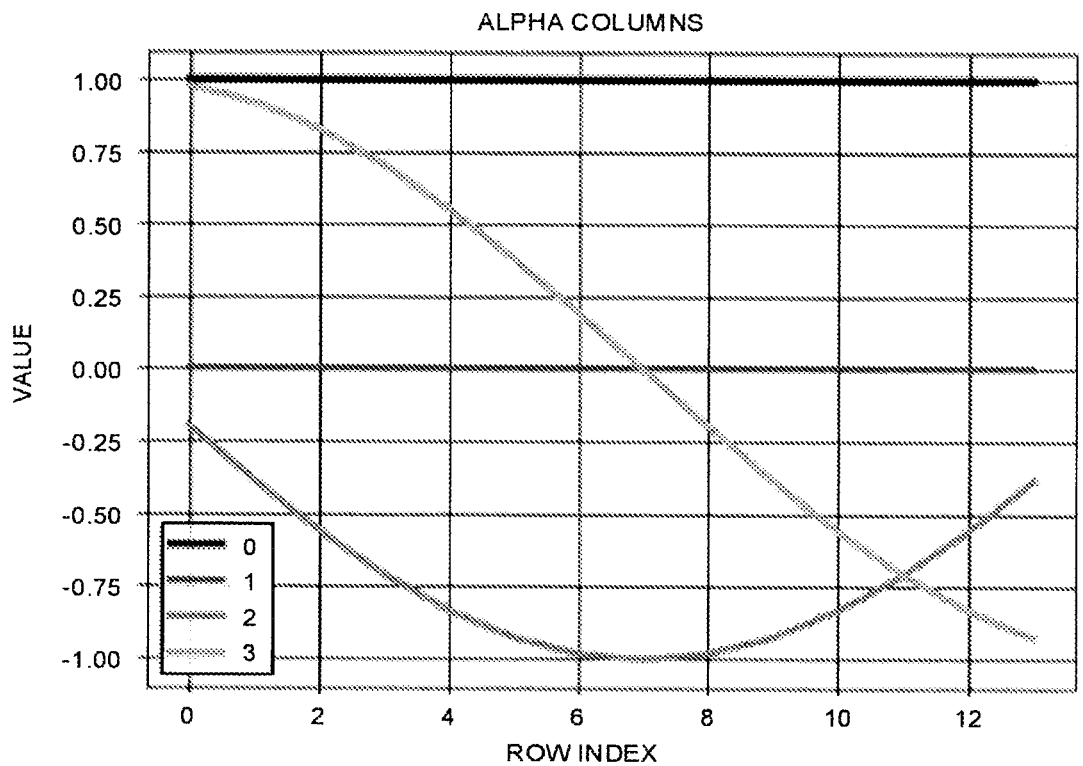
FIG. 14E illustrates one example of alpha columns.

FIG. 14E illustrates one example of alpha columns. FIG. 14E includes value versus row.

0.9 A and A # (Pseudoinverse) (e.g., 1314 of FIG. 13)

The A and A # (psedoinverse) matrices are generated using alpha and alpha transpose. These do not have signal data specific information and can be precomputed. The A # matrix is used in combination with baseline derived matrices W and F defined below to calculate the missing points estimates. Even (zero-based indices) correspond to generating the real values of the estimated missing points and odd indices imaginary values.
[19]: # Generate A Matrix
A=alpha.T@alpha
A[1, 1]=1.0
A_cond=np.linalg.cond(A)
print('A_cond=', A_cond)

Example

A_cond=39.60559675766955
[20]: print(A)

Example

[14. 0. −9.9581 0.9808]
[0. 1. 0. 0.]
[−9.9581 0. 7.9619 −0.1913]
[0.9808 0. −0.1913 6.0381]]
[21]: A_pinv=np.linalg.pinv(A, rcond=1.0e-9, hermitian=True)
A_pinv_cond=np.linalg.cond(A_pinv)
print('A_pinv_cond=', A_pinv_cond)

Example

A_pinv_cond=39.60559675766937
[22]: print(A_pinv)

Example

[[6.8766e−01 −1.4988e−15 8.5803e−01 −8.4509e−02]
[−1.4988e−15 1.0000e+00 −1.9213e−15 1.9262e−16]
[8.5803e−01 −1.9213e−15 1.1963e+00 −1.0146e−01]
[−8.4509e−02 1.9262e−16 −1.0146e−01 1.7613e−01]]

0.10 T Matrix (e.g., 1316 of FIG. 13)

The diagonal T matrix is generated, this selects baseline points from a projection.

[23]: t_vec=np.zeros((N,))
t_vec[:Nb]=1.0
t_vec_shift=int(Nb/2−round(zero_f_idx−(N/2)))
t_vec=np.roll(t_vec, −t_vec_shift)
[24]: print(t_vec)

Example

[1. 1. 1. 1. 1. 1. 1. 0. 0. 0. 0. 0. 0. 0. 0. 0. 0. 0. 0. 0. 0. 0. 0. 0. 1. 1. 1. 1. 1. 1. 1.]
[25]: T_mat=np.diag(t_vec)
print(T_mat)

Example

[[1. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 1. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 1. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 1. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 1. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 1. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 1. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 1. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 1. 0. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 1. 0. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 1. 0. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 1. 0. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 1. 0. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 1. 0.]
[0. 0. 0. 0. 0. 0. 0. 0. 0. 0. 0. 0. 0. 0. 0. 0. 0. 0. 0. 0. 0. 0. 0. 0. 0. 0. 0. 0. 0. 0. 1.]

0.11 G Matrix (e.g., 1318 of FIG. 13)

The G matrix is related to the A # matrix and is used for the phase (phi) estimation.

[26]: # Generate the G matrix
G=np.eye(Nb, dtype=np.double) −alpha@A_pinv@alpha.T print(G)

Example

[[0.5591 −0.3362 −0.2355 −0.1424 −0.0608 0.0064 0.0566 0.0877 0.0987 0.0891 0.0593 0.0103 −0.0558 −0.1366]
[−0.3362 0.7279 −0.2083 −0.1473 −0.0914 −0.0429 −0.0035 0.0253 0.0422 0.0467 0.0386 0.0182 −0.0136 −0.0558]
[−0.2355 −0.2083 0.8215 −0.1473 −0.1158 −0.0852 −0.0568 −0.0317 −0.0107 0.0053 0.0157 0.0201 0.0182 0.0103]
[−0.1424 −0.1473 −0.1473 0.8576 −0.1329 −0.1191 −0.1015 −0.0808 −0.0579 −0.0335 −0.0087 0.0157 0.0386 0.0593]
[−0.0608 −0.0914 −0.1158 −0.1329 0.8579 −0.143 −0.1357 −0.1203 −0.0975 −0.0682 −0.0335 0.0053 0.0467 0.0891]
[0.0064 −0.0429 −0.0852 −0.1191 −0.143 0.8438 −0.1581 −0.1486 −0.1282 −0.0975 −0.0579 −0.0107 0.0422 0.0987]
[0.0566 −0.0035 −0.0568 −0.1015 −0.1357 −0.1581 0.8321 −0.1647 −0.1486 −0.1203 −0.0808 −0.0317 0.0253 0.0877]
[0.0877 0.0253 −0.0317 −0.0808 −0.1203 −0.1486 −0.1647 0.8321 −0.1581 −0.1357 −0.1015 −0.0568 −0.0035 0.0566]
[0.0987 0.0422 −0.0107 −0.0579 −0.0975 −0.1282 −0.1486 −0.1581 0.8438 −0.143 −0.1191 −0.0852 −0.0429 0.0064]
[0.0891 0.0467 0.0053 −0.0335 −0.0682 −0.0975 −0.1203 −0.1357 −0.143 0.8579 −0.1329 −0.1158 −0.0914 −0.0608]
[0.0593 0.0386 0.0157 −0.0087 −0.0335 −0.0579 −0.0808 −0.1015 −0.1191 −0.1329 0.8576 −0.1473 −0.1473 −0.1424]
[0.0103 0.0182 0.0201 0.0157 0.0053 −0.0107 −0.0317 −0.0568 −0.0852 −0.1158 −0.1473 0.8215 −0.2083 −0.2355]
[−0.0558 −0.0136 0.0182 0.0386 0.0467 0.0422 0.0253 −0.0035 −0.0429 −0.0914 −0.1473 −0.2083 0.7279 −0.3362]

[−0.1366 −0.0558 0.0103 0.0593 0.0891 0.0987 0.0877 0.0566 0.0064 −0.0608 −0.1424 −0.2355 −0.3362 0.5591]]
[27]: G_cond=np.linalg.cond(G)
print('G_cond=', G_cond)

Example

G_cond=3.647593213023406e+16
[28]: #plt.figure( )
plt.imshow(G, label='G', cmap='gray')
plt.imshow(G, label='G')
plt.show( )

0.12 Prepare Baseline Region Data (e.g., 1320 of FIG. 13)

Signal region points in the complex projection are zeroed by the T matrix, leaving only baseline points with nonzero values. W consists of a vector containing only the complex Nb baseline points.
[29]: fid_pinv=fid_dist;
p_base=T_mat@p_dist
[30]: plt.figure(clear=True)
plt.title('Baseline, signal region zeroed')
plt.plot(p_base.real, label='Real')
plt.plot(p_base.imag, label='Imag')
plt.xlabel('Frequency Index')
plt.ylabel('Signal [arb]')
plt.legend( )
plt.show( )

Example

Figure 14F:
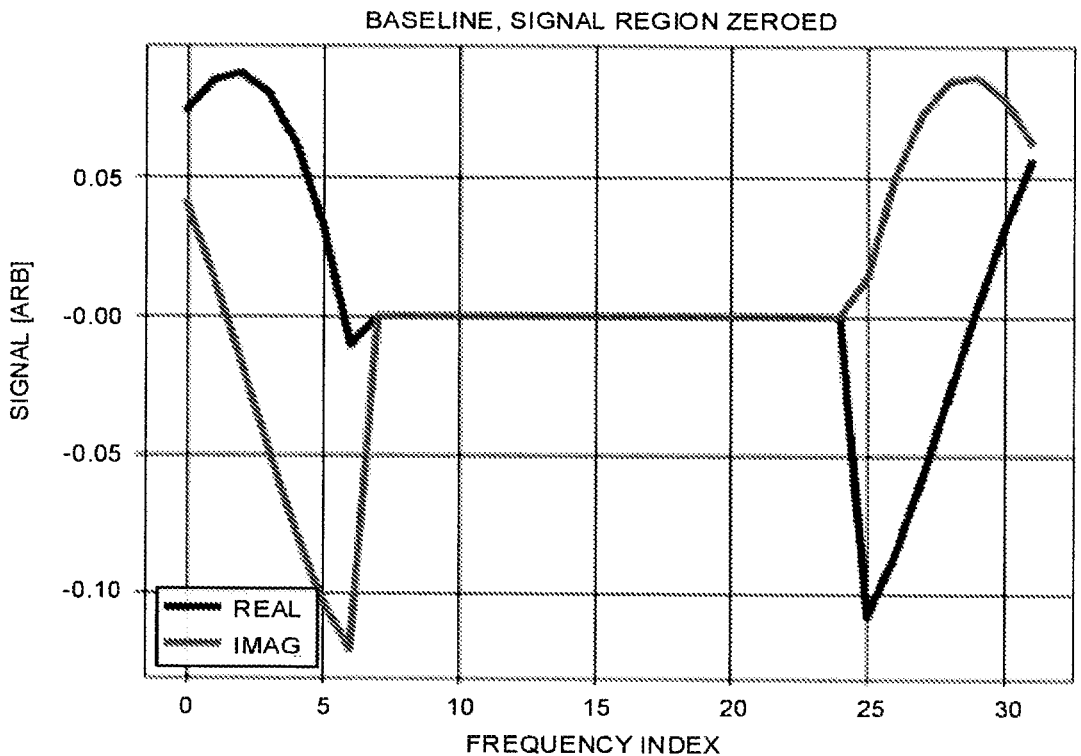
FIG. 14F illustrates one example of a baseline with signal region zeroed.

FIG. 14F illustrates one example of a baseline with signal region zeroed. FIG. 14F includes signal versus frequency for the real object and the imaginary object.
[31]: # Shift and Clip the Baseline Data
W=np.roll(p_base, t_vec_shift)
W=W[:Nb]
[32]: plt.figure(clear=True)
plt.title('Baseline Only, Shifted')
plt.plot(W.real, label='Real')
plt.plot(W.imag, label='Imag')
plt.xlabel('Index')
plt.ylabel('Baseline Signal [arb]')
plt.legend( )
plt.show( )

Example

Figure 14G:
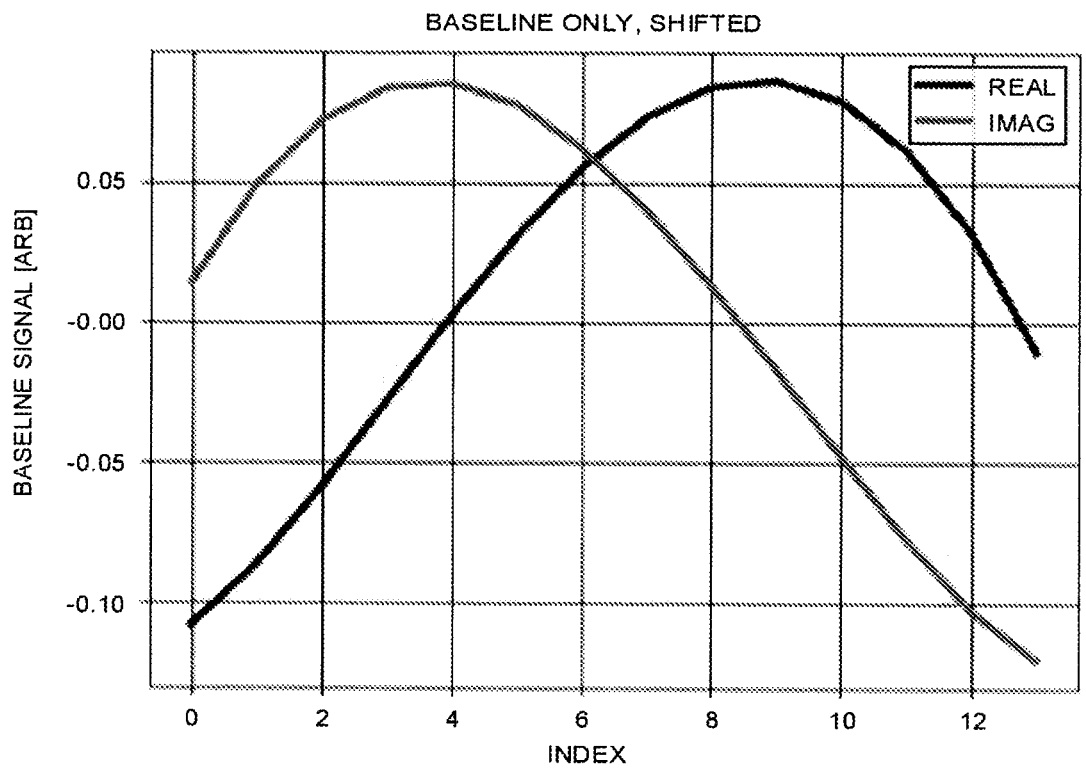
FIG. 14G illustrates one example of the baseline only shifted.

FIG. 14G illustrates one example of the baseline only shifted. FIG. 14G includes the baseline signal versus index for the real object and the imaginary object.

0.13 Estimate phi (Phase) by Minimizing Imaginary Component of the Baseline (e.g. 1322 of FIG. 13)

This consists of finding the roots of a polynomial with coefficients p and q determined by multiplying the G matrix by combinations of the real and imaginary components of the baseline points in W.
[33]: # Compute p and q
p=−G@W.real.T@W.imag
q=G@W.real.T@W.real−G@W.imag.T@W.imag

[34]: print('p=', p)
print('q=', q)

Example p=0.0011540296546748783
q=1.4039552952466346e−06
[35]: # Solve for tau
poly=np.polynomial. Polynomial([p, q, −p])
tau_all=poly.roots( )
[36]: print(poly)
print('tau_all=', tau_all)

Example $0.0011540296546748783 + 1.4039552952466346e{-}06 \cdot x^1 - 0.0011540296546748783 \cdot x^2$
tau_all=[−0.9994 1.0006]
[37]: if p>0:
tau=tau_all[1]
else:
tau=tau_all[0]
[38]: print('tau=', tau)

Example tau=1.000608468894717
[39]: # Compute phi
phi=np.arctan(tau)
[40]: phi_deg=phi*180/pi
print('phi_deg=', phi_deg)

Example phi_deg=45.017426047674675
[41]: phi_deg_error=phi_deg−phi_true_deg
print('phi_deg_error=', phi_deg_error)

Example phi_deg_error=0.01742604767467526

0.14 Estimate Missing Datapoints From phi Corrected Baseline, F_e, Alpha and A_pinv (e.g., 1324 of FIG. 13)

The real and imaginary components (as a real vector) of the missing FID points are calculated by first forming the vector F_re consisting of the real component of the phase corrected baseline points. These are multiplied by alpha (which consists of the Fourier basis function for that coefficient of the FID). The vector f_re is then the estimate for those components in the baseline. Finally the missing points as a real valued vector are calculated by multiplying by −A_pinv (−A #) which are the real and imaginary coefficients of missing points that minimize the integrated real signal in the phase corrected baseline reason of the projection (F_re). These are placed in complex form to be joined with the rest of the valid data by taking the even index values of dm_re as the real part and odd index values as the imaginary part.

[42]: # Estimate Missing Datapoints
F_re=np.real(np.exp(-1j*phi)*W)
F_re=np.real(W) # debugging, no phi correction
f_re=alpha.T@F_re
dm_re=-A_pinv@f_re
[43]: print(dm_re)

Example

[1.4566e-01 -3.3671e-16 2.2610e-01 -3.6085e-02]
[44]: # Convert to Complex
dm=np.zeros((Nd,), dtype=np.complex64);
for idx in np.arange(Nd):
re_idx=2*idx;
im_idx=2*idx+1;
dm[idx]=dm_re[re_idx]+1j*dm_re[im_idx]
[45]: Print(dm)

Example

[0.1457-3.3671e-16j 0.2261-3.6085e-02j]

0.15 Set Up the Estimated FID (e.g., 1326 of FIG. 13)

The final step is to combine the estimated points with the rest of the valid FID data.
[46]: # Set Up the Estimated fid
fid_pinv[:Nd]=np.exp(1j*phi)*dm
if apply_phi:
    pass
else:
    fid_pinv=np.exp(-1j*phi)*fid_pinv
[47]: plt.figure(clear=True)
plt.title('FID with Estimated Missing Points:\n phase difference from COM shift')
plt.plot(fid_pinv.real[0:N_show], label='Real')
plt.plot(fid_pinv.imag[0:N_show], label='Imag')
plt.xlabel('Time Index')
plt.ylabel('Signal [arb]')
plt.legend( )
plt.show( )

Example

Figure 14H:
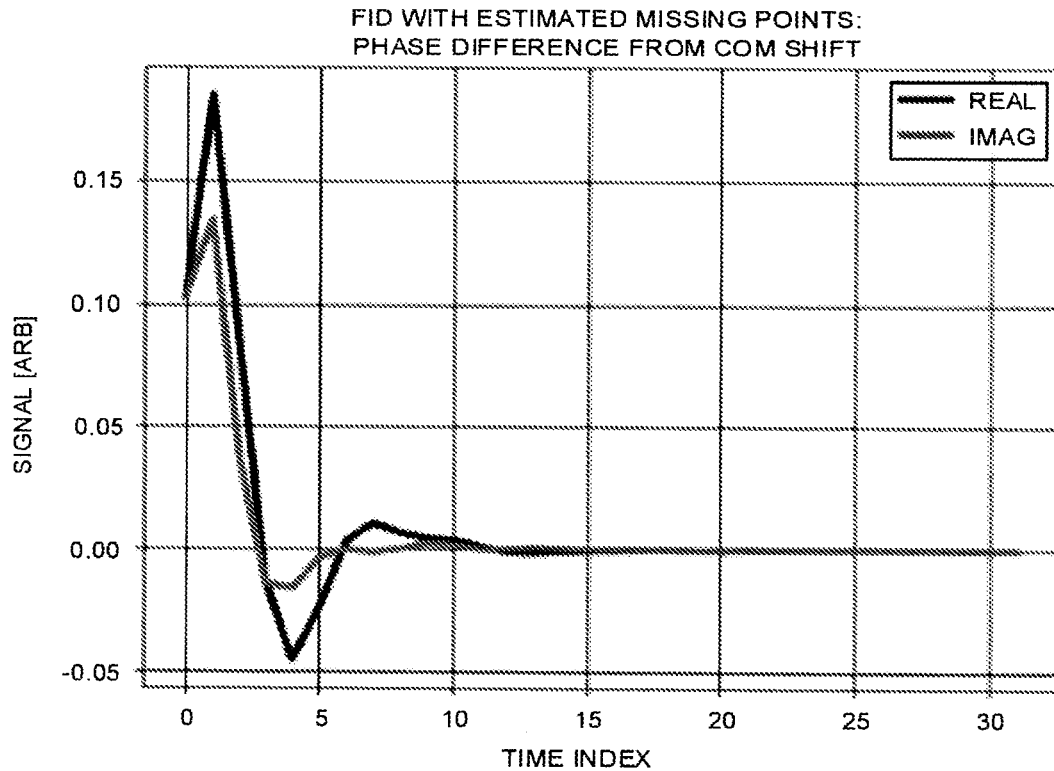
FIG. 14H illustrates one example of an estimated FID with missing points.

FIG. 14H illustrates one example of an estimated FID with missing points with phase difference from COM shift. FIG. 14H includes signal versus time for the real object and the imaginary object.

0.16 Estimated Projection, Shifted Back to Original Position

This and subsequent steps are intended to show the estimate produces low error when the object signal is properly excluded from the baseline and the condition number position of A and A # are less than $10^{-4}$.
[48]: # Corrected Projection
p_pinv=fft.fftshift(fft.fft(fid_pinv))
[49]: # Corrected Projection
p_pinv=fft.fftshift(fft.fft(fid_pinv))
p_pinv=np.roll(p_pinv, p_com_shift)
[54]: plt.figure(clear=True)
plt.title('Estimated Projection')
plt.plot(p_pinv.real, label='Real')
plt.plot(p_pinv.imag, label='Real')
plt.xlabel('Frequency Index')
plt.ylabel('Signal [arb]')
plt.legend( )
plt.show( )

Example

Figure 14I:
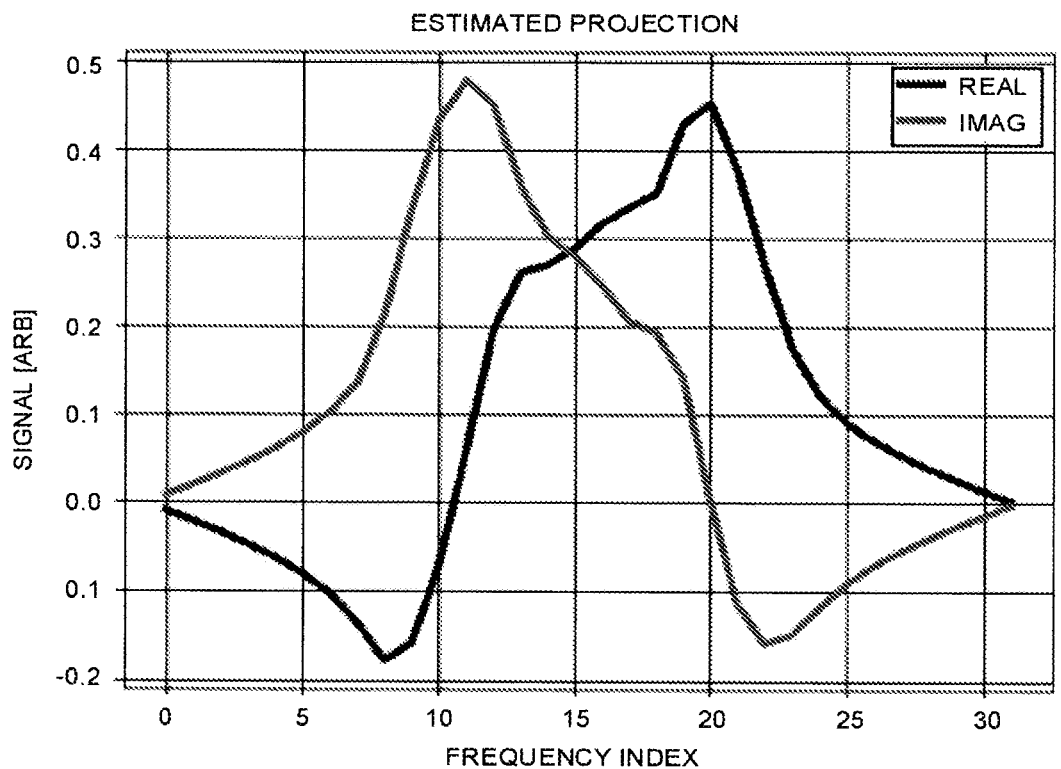
FIG. 14I illustrates one example of an estimated projection for the estimated FID of FIG. 14H.

FIG. 14I illustrates one example of an estimated projection for the estimated FID of FIG. 14H. FIG. 14I includes signal versus frequency for the real object and the imaginary object.

0.17 Estimated Projection, Difference From True

[50]: plt.figure(clear=True)
plt.title('Estimated Projection, Difference From True')
plt.plot(p_pinv.real-p_true.real, label='Real')
plt.plot(p_pinv.imag-p_true.imag, label='Real')
plt.xlabel('Frequency Index')
plt.ylabel('Signal Difference [arb]')
plt.legend( )
plt.show( )

Example

Figure 14J:
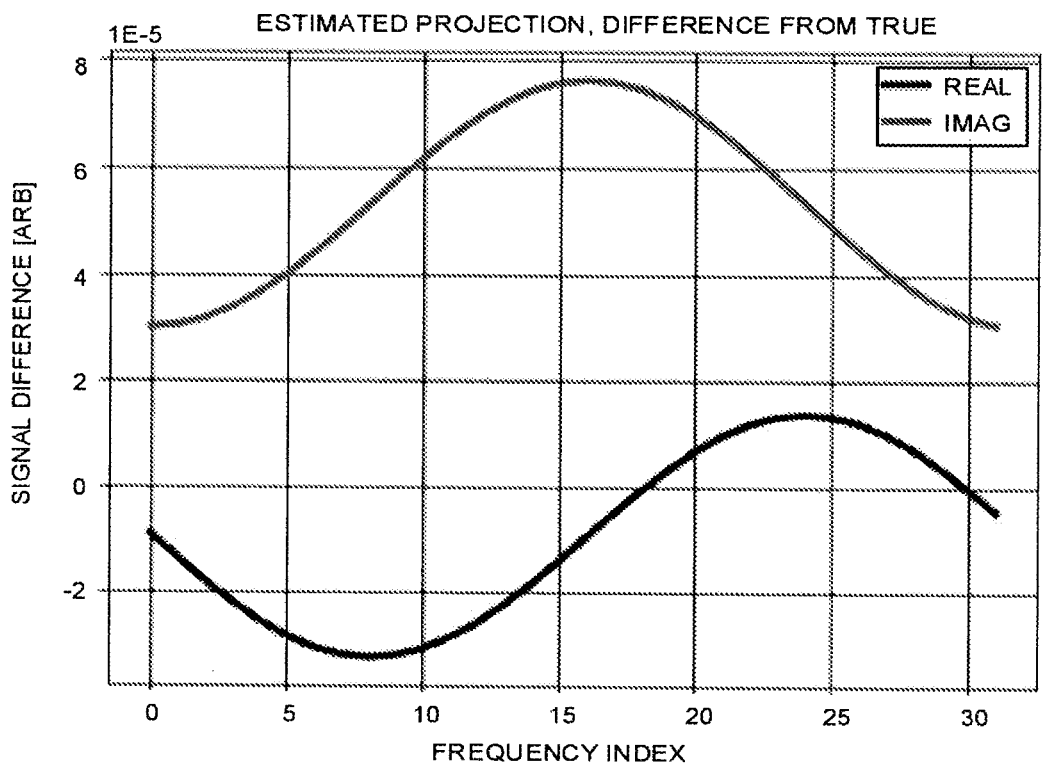
FIG. 14J illustrates one example of an estimated projection difference from true.

FIG. 14J illustrates one example of an estimated projection difference from true.
FIG. 14J includes signal difference versus frequency for the real object and the imaginary object.

0.18 COM Shift Corrected FID

[51]: fid_pinv=fft.ifft(fft.ifftshift(p_pinv))
[52]: plt.figure(clear=True)
plt.title('COM Shift corrected FID')
plt.plot(fid_pinv.real[0:N_show], label='Real')
plt.plot(fid_pinv.imag[0:N_show], label='Imag')
plt.xlabel('Time Index')
plt.ylabel('Signal [arb]')
plt.legend( )
plt.show( )

Example

Figure 14K:
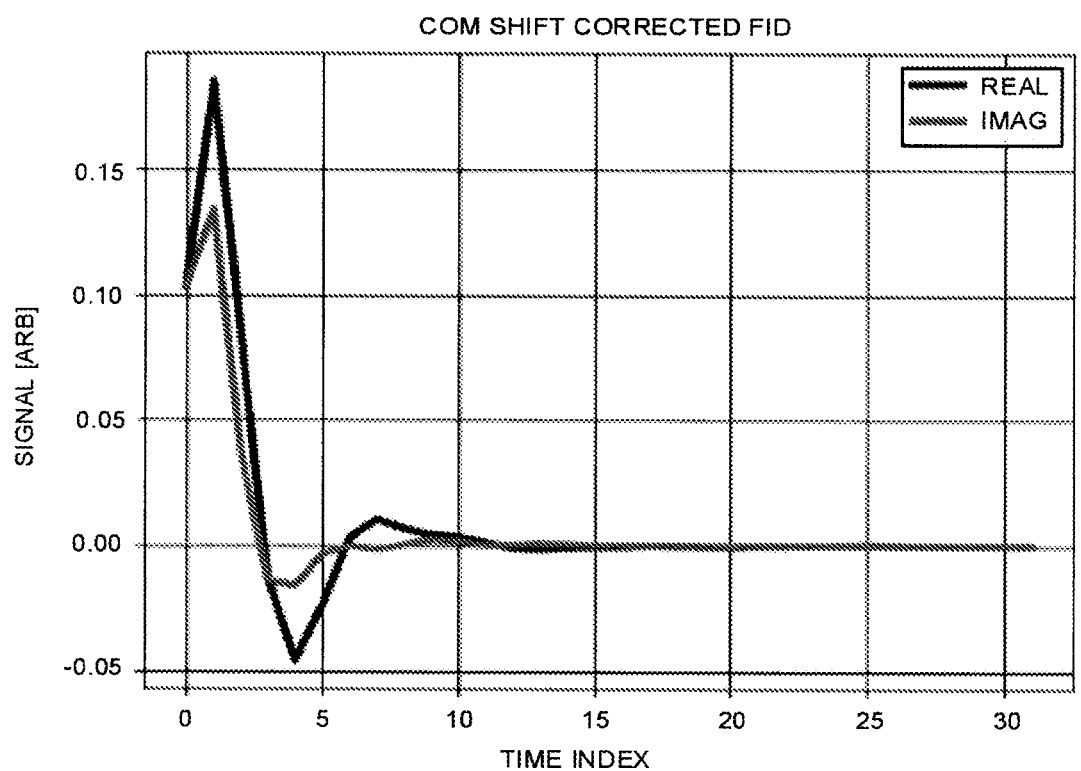
FIG. 14K illustrates one example of a COM shift corrected FID.

FIG. 14K illustrates one example of a COM shift corrected FID. FIG. 14K includes signal versus time for the read object and the imaginary object.
[53]: plt.figure(clear=True)
plt.title('Estimated FID difference from True')
plt.plot(fid_pinv.real[0:N_show]-fid_true.real[0:N_show], label='Real')
plt.plot(fid_pinv.imag[0:N_show]-fid_true.imag[0:N_show], label='Imag')
plt.xlabel('Time Index')
plt.ylabel('Signal Difference [arb]')
plt.legend( )
plt.show( )

Example

Figure 14L:
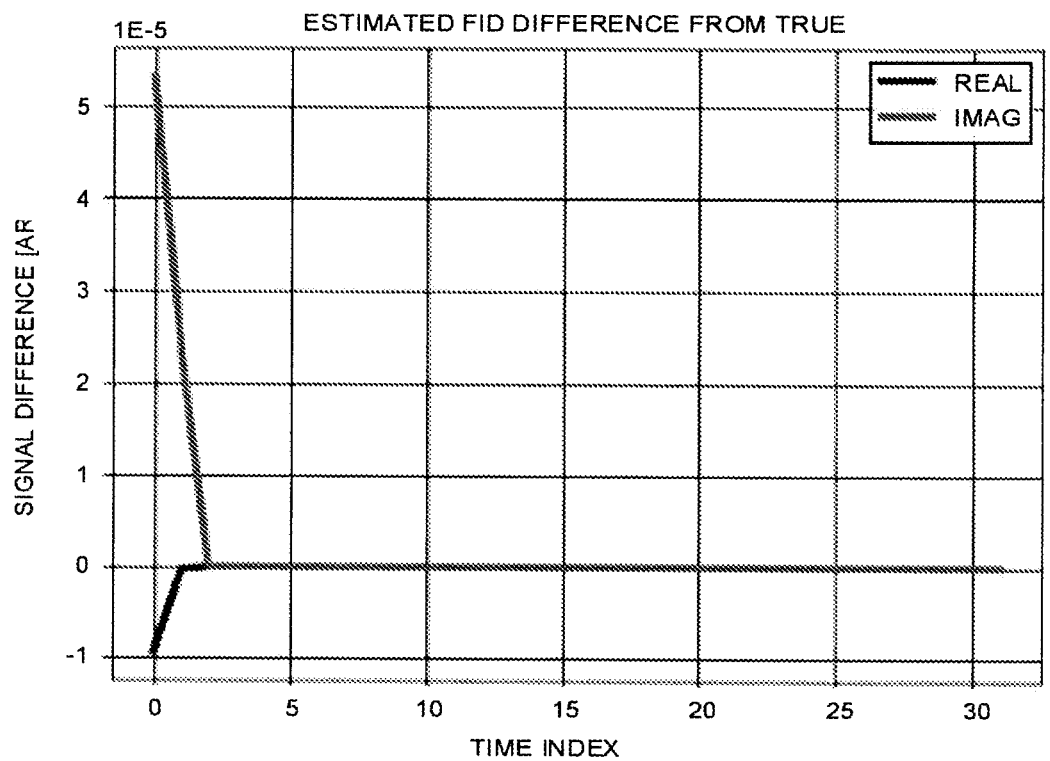
FIG. 14L illustrates one example of estimated FID difference from True.

FIG. 14L illustrates one example of estimated FID difference from True. FIG. 14L includes signal difference versus time for the real object and the imaginary object.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

The invention claimed is:

1. A non-transitory machine-readable storage medium storing instructions; and
a processor to execute the instructions to:
receive magnetic resonance imaging (MRI) data of a patient obtained via a free induction decay (FID) sequence, with a single or plurality of channels and gradient directions, each FID of the FID sequence indicating missing or corrupted points at the beginning of the FID;
replace the missing or corrupted points of each FID with estimated points to generate a corrected FID sequence; and
estimate a phase that minimizes an imaginary DC value of each corresponding FID.

2. A method for estimating missing points and phase estimation for free induction decay (FID) sequences, the method comprising:
loading, via a processing system, FID sequence data containing a single or plurality of channels and gradient directions;
setting, via the processing system, the missing or corrupted points of the FID data to zero;
generating, via the processing system, a distorted projection of the FID data with the missing points set to zero;
estimating, via the processing system, a magnitude center of mass of the distorted projection;
preparing, via the processing system, baseline region data;
estimating, via the processing system, a phase of the FID data based on the baseline region data;
estimating, via the processing system, missing points from a phase corrected baseline; and
determining, via the processing system, estimated FID data including the estimated missing points.

3. A system comprising:
a non-transitory machine-readable storage medium storing instructions; and
a processor to execute the instructions to:
receive magnetic resonance imaging (MRI) data of a patient obtained via a MRI sequence with a single or plurality of channels and gradient directions, each free induction decay (FID), echo, or partial echo of the MRI sequence including missing or corrupted points;
replace the missing or corrupted points of each FID, echo, or partial echo with estimated points to generate corrected data; and
estimate a phase that minimizes an imaginary DC value of each corrected set of datapoints.

4. A method for estimating missing points and phase estimation for MRI sequences, the method comprising:
loading, via a processing system, MRI data from at least one free induction decay (FID), gradient echo, or spin echo containing a single or plurality of channels and gradient directions;
setting, via the processing system, the missing or corrupted points of the MRI data to zero;
generating, via the processing system, a distorted projection of the MRI data with the missing points set to zero;
estimating, via the processing system, a magnitude center of mass of the distorted projection;
preparing, via the processing system, baseline region data;
estimating, via the processing system, a phase of the MRI data based on the baseline region data;
estimating, via the processing system, missing points from a phase corrected baseline; and
determining, via the processing system, estimated MRI data including the estimated missing points.

5. The system of claim 1, wherein the processor executes the instructions to replace the missing or corrupted points by an estimate from the uncorrupted points.

6. The system of claim 1, wherein the processor executes the instructions to estimate the phase by minimizing a magnitude of a baseline region in a projection.

7. The system of claim 1, wherein the FID sequence comprises a sweep imaging with Fourier transformation (SWIFT) sequence or a zero echo time (ZTE) sequence.

8. The system of claim 1, wherein a bandwidth of the ZTE sequence is greater than or equal to 62.5 kHz.

9. The system of claim 1, further comprising:
a transmit coil;
a receiver coil; and
a proton free polymer housing enclosing the transmit coil and the receiver coil.

10. The method of claim 2, further comprising:
generating, via the processing system, an alpha matrix based on a number of missing points, a number of baseline points, and the center of mass;
generating, via the processing system, A and A # matrices using alpha and alpha transpose;
generating, via the processing system, a T matrix for selecting baseline points from a projection; and
generating, via the processing system, a G matrix for the phase estimation,
wherein preparing the baseline region data comprises preparing the baseline region data using the T matrix, and
wherein estimating the phase comprises minimizing an imaginary component of the baseline using the G matrix.

11. The method of claim 2, further comprising:
setting, via the processing system, parameters including a number of points in the FID sequence, a number of missing points to be estimated, and a number of baseline points to use,
wherein setting the missing points of the FID sequence to zero comprises setting the missing points of the FID sequence to zero based on the parameters.

12. The method of claim 2, wherein generating the distorted projection comprises generating the distorted projection by Fourier transformation.

13. The system of claim 3, wherein the processor executes the instructions to replace the missing or corrupted points by an estimate from the uncorrupted points.

14. The system of claim 3, wherein the processor executes the instructions to estimate the phase by minimizing a magnitude of a baseline region in a projection.

15. The system of claim 3, wherein the MRI sequence comprises a sweep imaging with Fourier transformation (SWIFT) sequence or a zero echo time (ZTE) sequence.

16. The system of claim 3, wherein the MRI sequence comprises at least one free induction decay (FID), gradient echo, or spin echo.

17. The system of claim 3, wherein a bandwidth of the MRI sequence is greater than or equal to 62.5 kHz.

18. The system of claim 1, further comprising:
a transmit coil;
a receiver coil; and a proton free polymer housing enclosing the transmit coil and the receiver coil.

19. The method of claim 4, further comprising:

generating, via the processing system, an alpha matrix based on a number of missing points, a number of baseline points, and the center of mass;

generating, via the processing system, A and A # matrices using alpha and alpha transpose;

generating, via the processing system, a T matrix for selecting baseline points from a projection; and generating, via the processing system, a G matrix for the phase estimation, wherein preparing the baseline region data comprises preparing the baseline region data using the T matrix, and wherein estimating the phase comprises minimizing an imaginary component of the baseline using the G matrix.

20. The method of claim 4, further comprising:

setting, via the processing system, parameters including a number of points of acquired data, a number of missing points to be estimated, and a number of baseline points to use, wherein setting the missing points of the MRI data to zero comprises setting, based on the parameters, the missing points of the MRI data to zero.

* * * * *